US008672860B2

(12) United States Patent
Moore et al.

(10) Patent No.: US 8,672,860 B2
(45) Date of Patent: Mar. 18, 2014

(54) TETHERLESS BIOPSY DEVICE WITH SELF-REVERSING CUTTER DRIVE MECHANISM

(75) Inventors: Kyle P. Moore, Mason, OH (US); Haresh D. Patil, Dhule (IN); Michael J. Andreyko, Cincinnati, OH (US); Shailendra K. Parihar, Mason, OH (US); Eric B. Smith, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 813 days.

(21) Appl. No.: 12/467,365

(22) Filed: May 18, 2009

(65) Prior Publication Data

US 2010/0292607 A1 Nov. 18, 2010

(51) Int. Cl.
*A61B 5/00* (2006.01)

(52) U.S. Cl.
USPC ............................................. 600/567

(58) Field of Classification Search
USPC .................. 600/566, 564, 567, 568
See application file for complete search history.

(56) References Cited

U.S. PATENT DOCUMENTS

| | | | |
|---|---|---|---|
| 5,526,822 A | 6/1996 | Burbank et al. | |
| 5,669,394 A | 9/1997 | Bergey et al. | |
| 6,086,544 A | 7/2000 | Hibner et al. | |
| 6,626,849 B2 | 9/2003 | Huitema et al. | |
| 7,442,171 B2 | 10/2008 | Stephens et al. | |
| 7,922,737 B1 * | 4/2011 | Cesarini et al. | 606/170 |
| 8,192,353 B2 * | 6/2012 | Smith | 600/114 |
| 2006/0074345 A1 * | 4/2006 | Hibner | 600/566 |
| 2007/0032742 A1 | 2/2007 | Monson et al. | |
| 2007/0149894 A1 | 6/2007 | Heske et al. | |
| 2007/0255173 A1 | 11/2007 | Hibner | |
| 2008/0195066 A1 | 8/2008 | Speeg et al. | |
| 2008/0214955 A1 | 9/2008 | Speeg et al. | |
| 2008/0228103 A1 | 9/2008 | Ritchie et al. | |

OTHER PUBLICATIONS

U.S. Appl. No. 11/964,811, filed Dec. 27, 2008, Hibner.
U.S. Appl. No. 12/335,578, filed Dec. 16, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
U.S. Appl. No. 12/337,997, filed Dec. 18, 2008, Parihar.
U.S. Appl. No. 60/869,736, filed Dec. 13, 2006, Ritchie.
U.S. Appl. No. 60/874,792, filed Dec. 13, 2006, Hibner.

* cited by examiner

*Primary Examiner* — Max Hindenburg
(74) *Attorney, Agent, or Firm* — Frost Brown Todd LLC

(57) ABSTRACT

A biopsy device comprises a body, a needle, and a cutter. A self-reversing cutter translation mechanism translates the cutter proximally and distally in response to rotation of the cutter in a single rotational direction. The cutter translation mechanism comprises a lead screw with discretely formed threads and a rotatable pawl. The cutter is translated proximally when the pawl is in a first rotational orientation; and distally when the pawl is in a second rotational orientation. Resilient members cause the pawl to be rotated between the first and second rotational orientations when the cutter reaches a distal position and a proximal position. A vacuum draws severed tissue samples through the interior of the cutter to deposit the samples in a holder. The translation mechanism engages a valve mechanism to provide simultaneous venting to part of the needle and reversal of the pawl orientation when the cutter reaches a distal position.

20 Claims, 21 Drawing Sheets

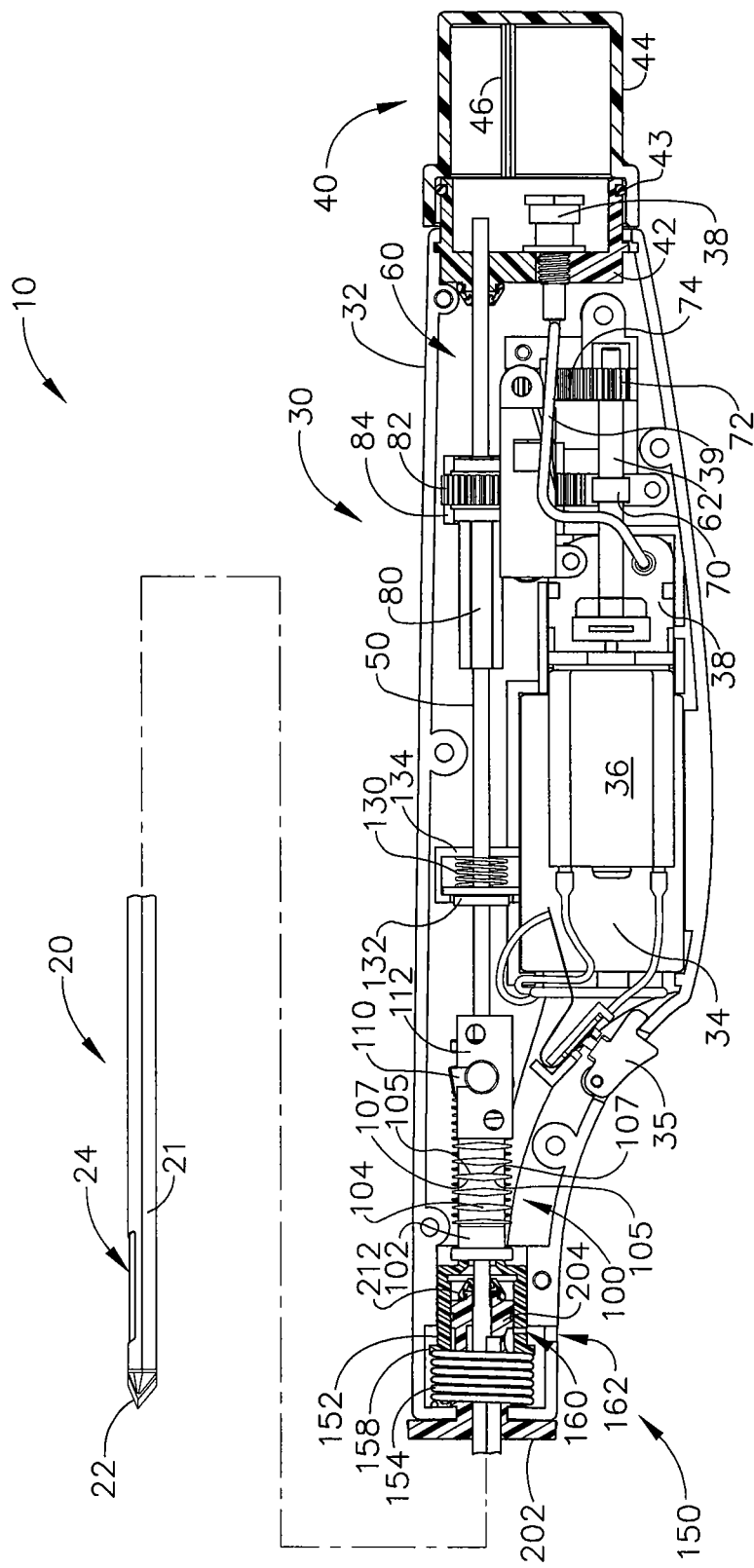

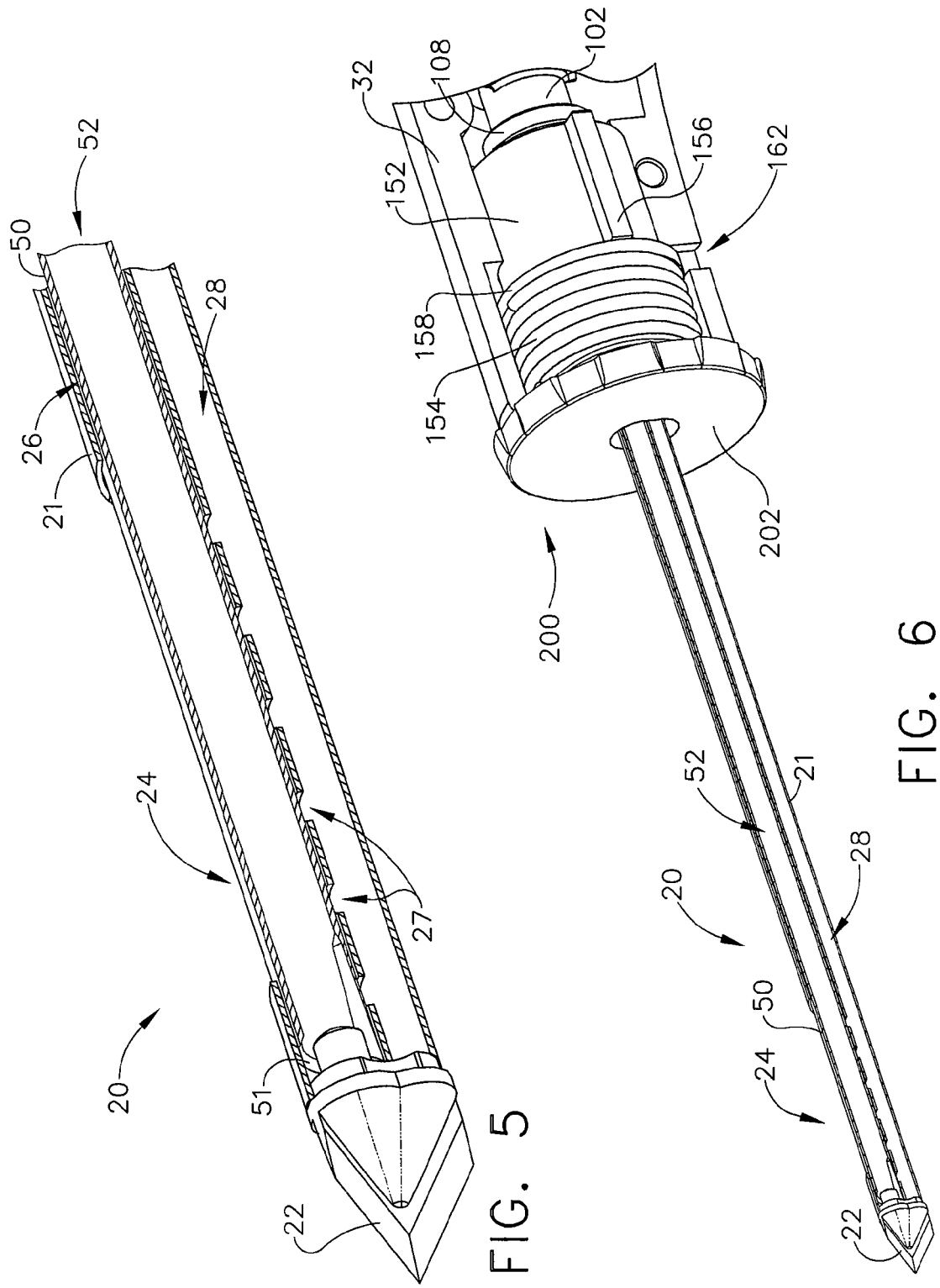

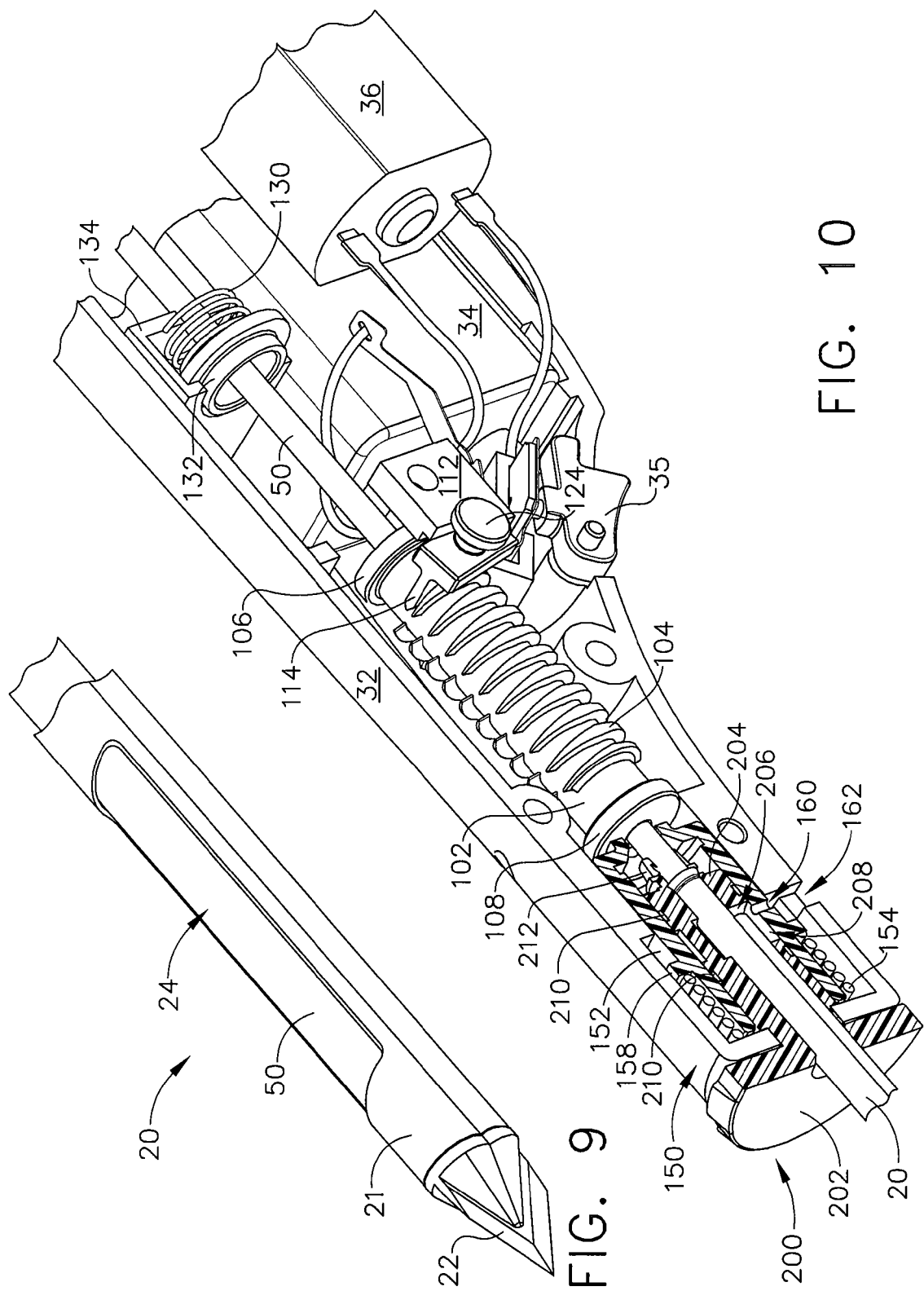

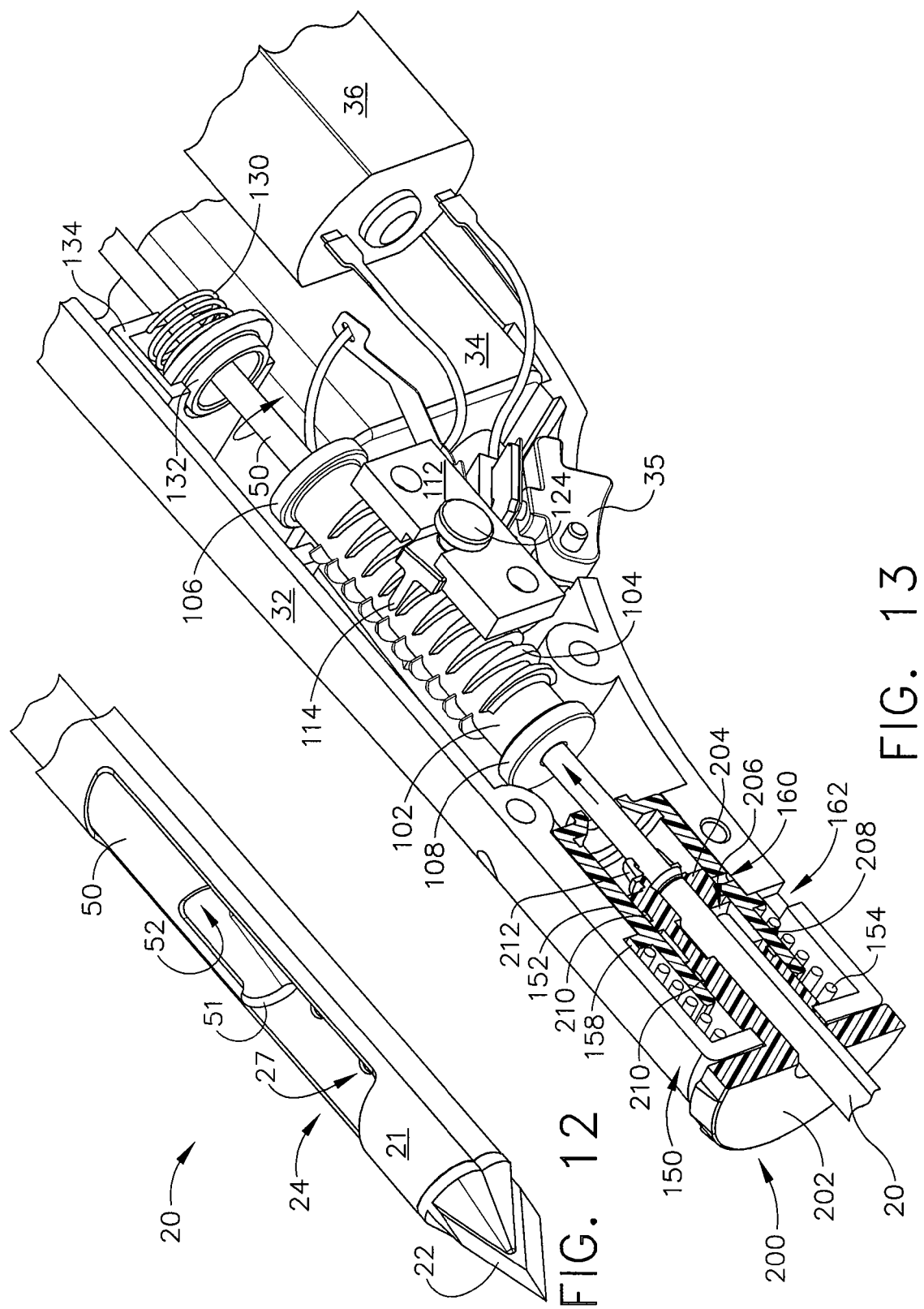

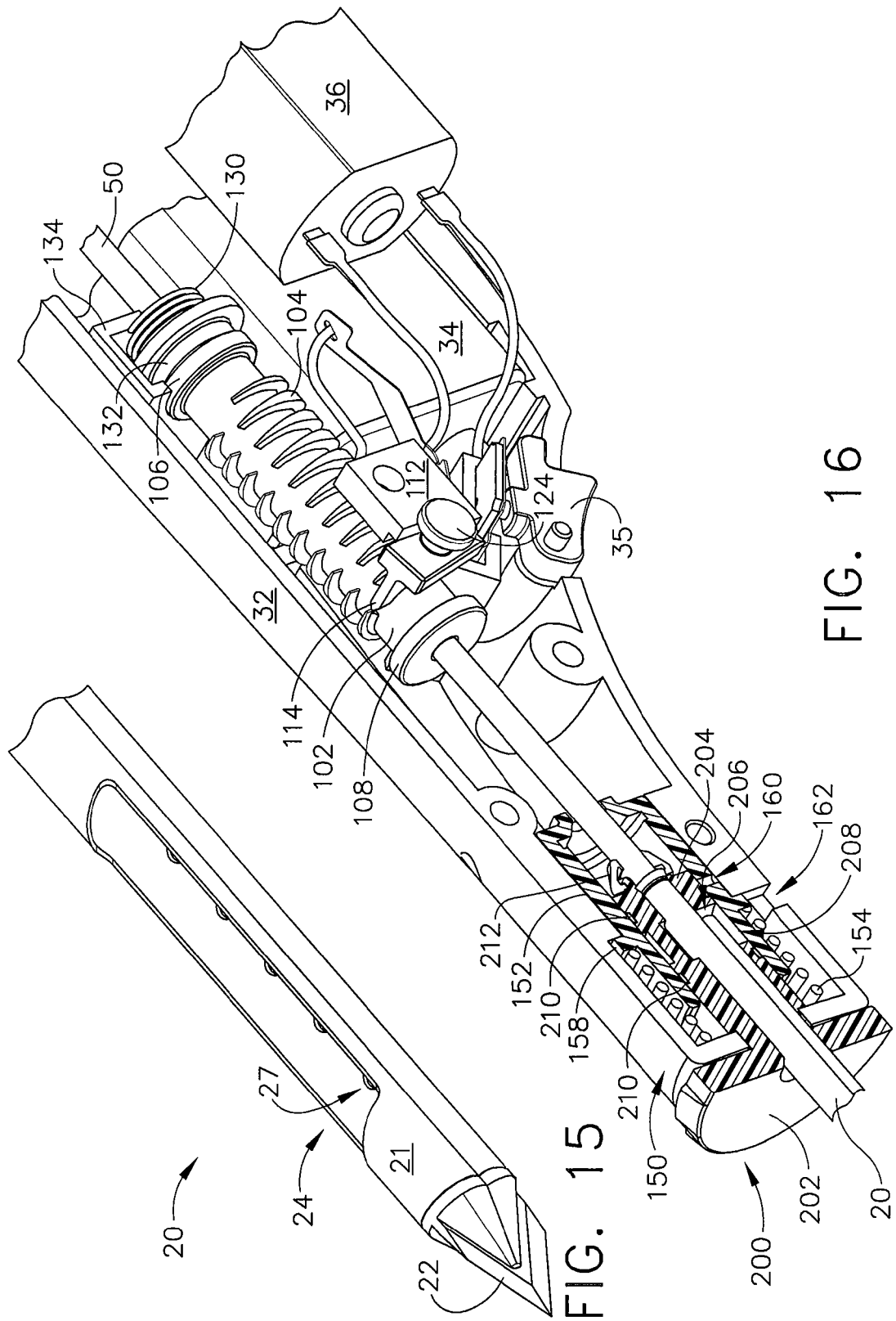

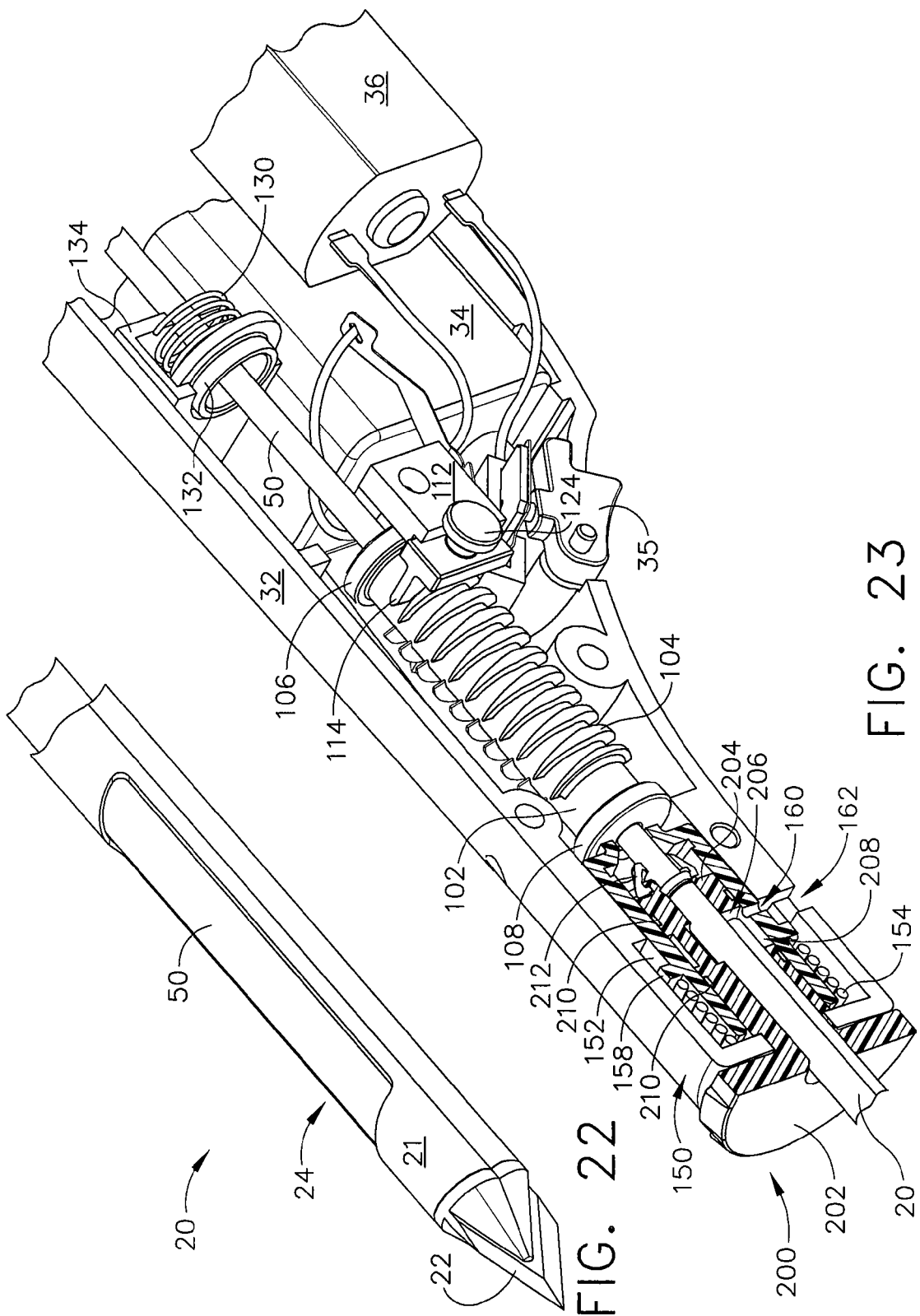

TETHERLESS BIOPSY DEVICE WITH SELF-REVERSING CUTTER DRIVE MECHANISM

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Non-Provisional patent application Ser. No. 11/964,811, entitled "Clutch and Valving System for Tetherless Biopsy Device," filed Dec. 27, 2007; U.S. Non-Provisional patent application Ser. No. 12/335,578, entitled "Hand Actuated Tetherless Biopsy Device with Pistol Grip," filed Dec. 16, 2008; and U.S. Non-Provisional patent application Ser. No. 12/337,942, entitled "Biopsy Device with Central Thumbwheel," filed Dec. 18, 2008. The disclosure of each of the above-cited U.S. Patents, U.S. Patent Application Publications, and U.S. Non-Provisional Patent Application is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4 depicts a side view of the biopsy device of FIG. 1, with a housing component removed and with a tissue sample holder cup in cross-section;

FIG. 5 depicts a partial cross-sectional view of the needle and cutter of the biopsy device of FIG. 1;

FIG. 6 depicts a partial perspective view of the distal portion of the biopsy device of FIG. 1, with the needle and cutter shown in cross-section;

FIG. 9 depicts a partial view of the needle of the biopsy device of FIG. 1, with the cutter at a distal starting position;

FIG. 10 depicts a partial side view of a central portion of the biopsy device of FIG. 1, with a housing component removed, with a valve assembly shown in cross-section, and with the cutter at the starting position of FIG. 9;

FIG. 12 depicts a partial view of the needle of the biopsy device of FIG. 1, with the cutter in an intermediate position between a distal starting position and a proximal retracted position, as the cutter is being retracted;

FIG. 13 depicts a partial side view of a central portion of the biopsy device of FIG. 1, with a housing component removed, with a valve assembly shown in cross-section, and with the cutter at the intermediate position of FIG. 12, as the cutter is being retracted;

FIG. 15 depicts a partial view of the needle of the biopsy device of FIG. 1, with the cutter in a proximal retracted position;

FIG. 16 depicts a partial side view of a central portion of the biopsy device of FIG. 1, with a housing component removed, with a valve assembly shown in cross-section, and with the cutter at the retracted position of FIG. 15;

FIG. 22 depicts a partial view of the needle of the biopsy device of FIG. 1, with the cutter at a distal advanced position;

FIG. 23 depicts a partial side view of a central portion of the biopsy device of FIG. 1, with a housing component removed, with a valve assembly shown in cross-section, and with the cutter at the advanced position of FIG. 22;

Figure 1:
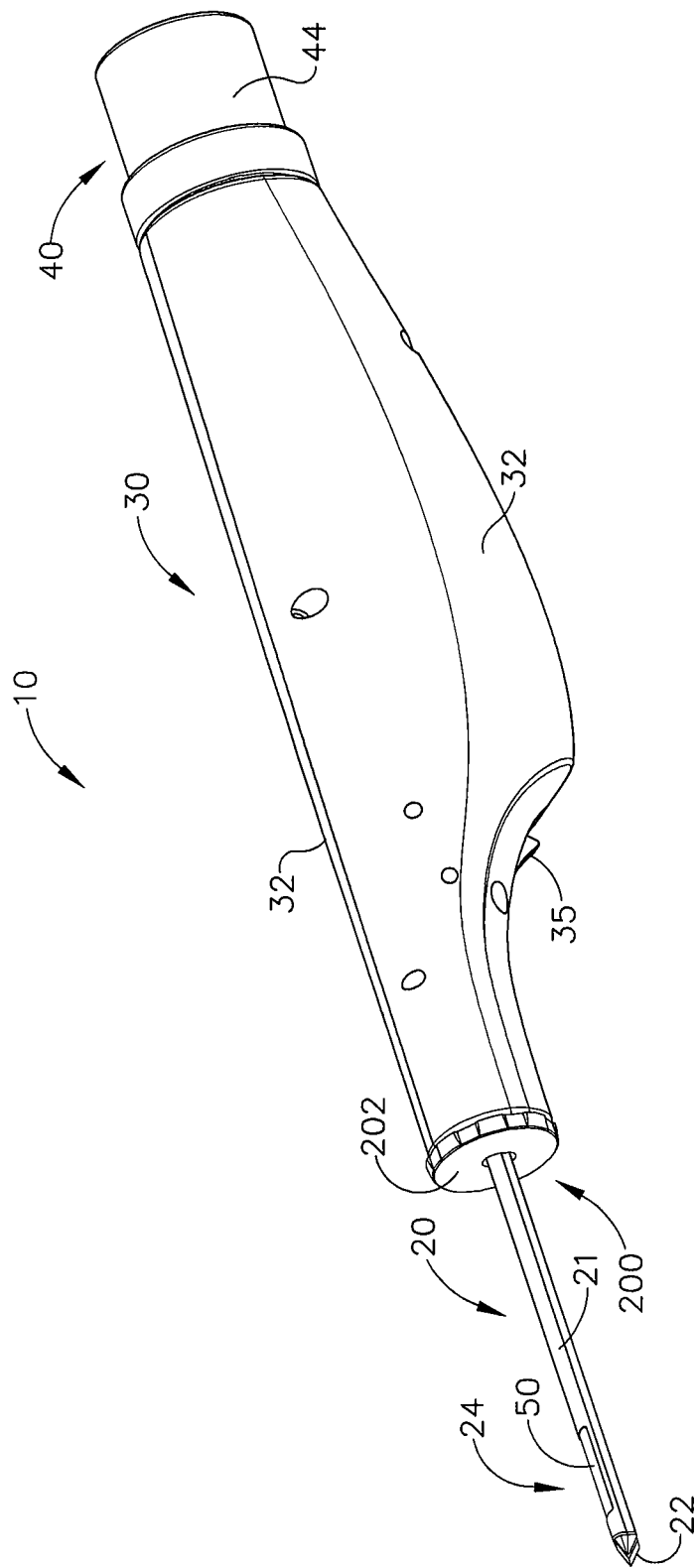
FIG. 1 depicts a perspective view of an exemplary tetherless biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

As shown in FIGS. 1-4, an exemplary biopsy device (10) comprises a needle (20), a body (30), and a tissue sample holder (40). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, and as described in greater detail below, a user may grasp body (30) with a single hand, insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) in the patient's breast. Such tissue samples may be pneumatically deposited in tissue sample holder (40), as described in greater detail below, then retrieved from tissue sample holder (40) for analysis. While examples described herein refer to the acquisition of biopsy samples from a patient's breast, it should be understood that biopsy device (10) may be used in a variety of other procedures for a variety of other purposes and in a variety of other parts of a patient's anatomy.

Exemplary Needle

As shown in FIGS. 5-6, needle (20) comprises a cannula (21) with a tissue piercing tip (22), a lateral aperture (24), a first lumen (26), and a second lumen (28). Tissue piercing tip (22) is configured to pierce and penetrate tissue, without requiring a high amount of force, and without requiring an opening to be pre-formed in the tissue prior to insertion of tip (22). A cutter (50) is disposed in first lumen (26), and is operable to rotate and translate within first lumen (26) as will be described in greater detail below. Lateral aperture (24) is located proximal to tip (22), is in fluid communication with first lumen (26), and is configured to receive tissue when needle (20) is inserted in a breast and when a cutter (50) is retracted as will also be described in greater detail below. A plurality of openings (27) provide fluid communication between first and second lumens (26, 28). A plurality of external openings (not shown) may also be formed in needle (20), and may be in fluid communication with second lumen (28). Examples such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

Figure 2:
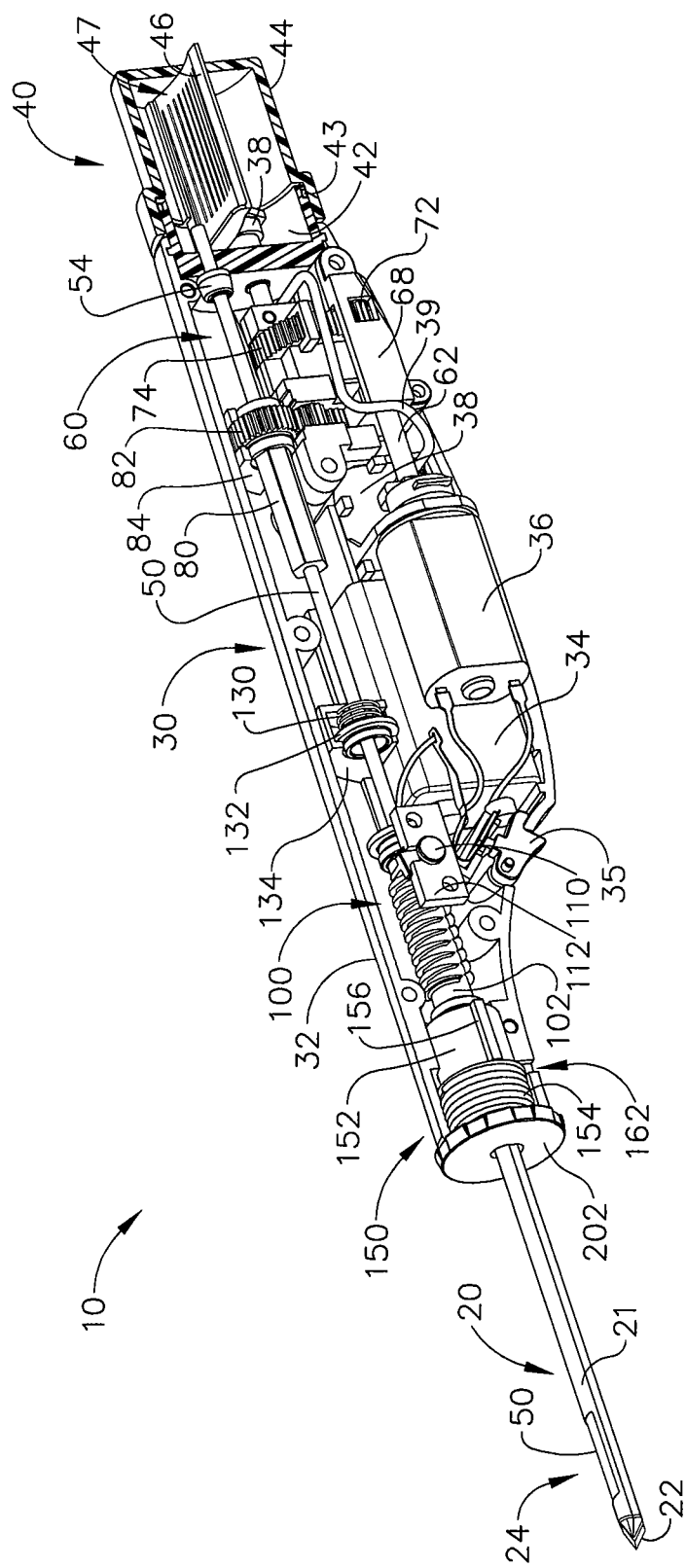
FIG. 2 depicts a perspective view of the biopsy device of FIG. 1, with a housing component removed and with a tissue sample holder cup in cross-section.
Figure 3:
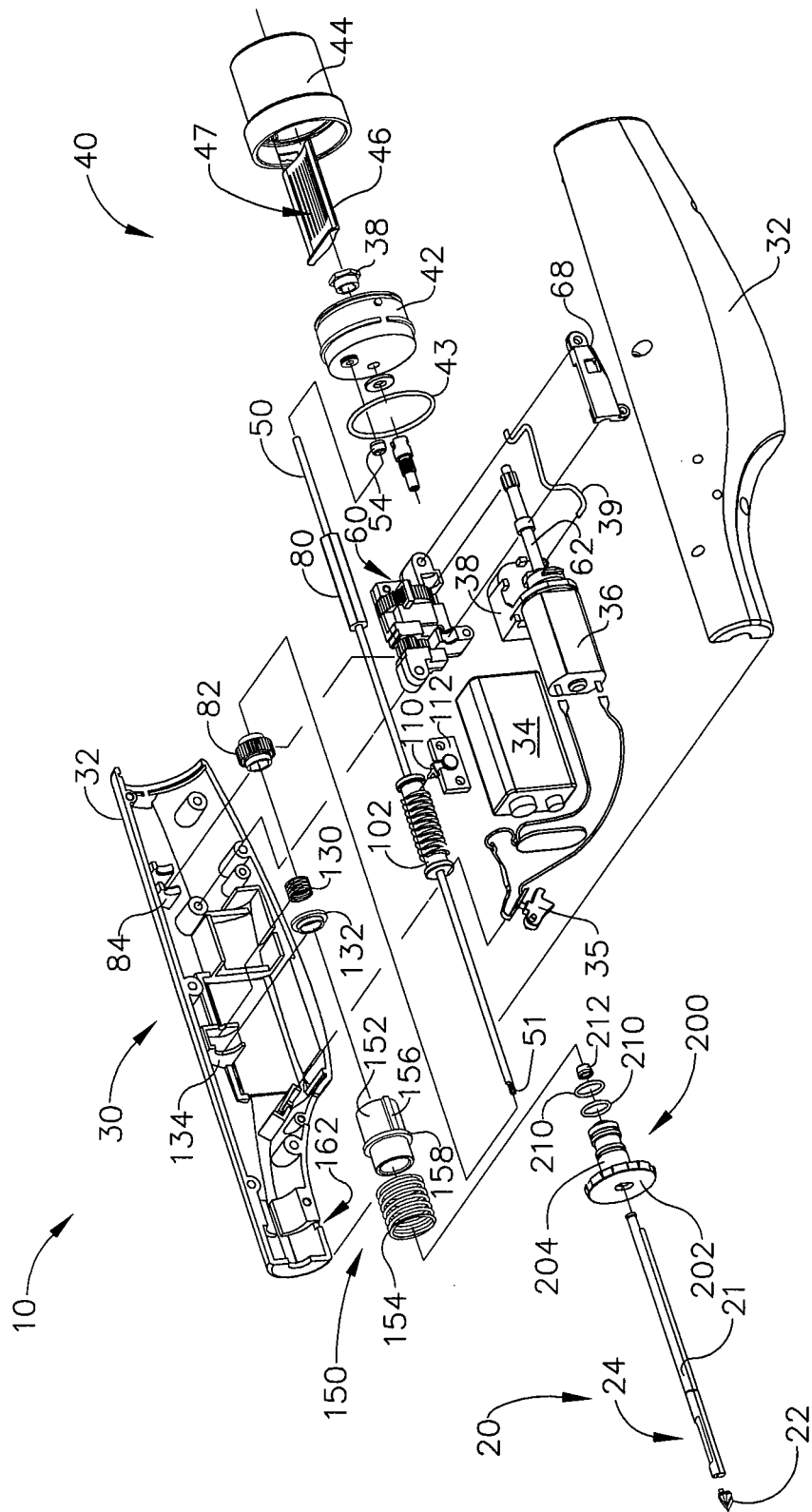
FIG. 3 depicts an exploded perspective view of the biopsy device of FIG. 1.
Figure 7:
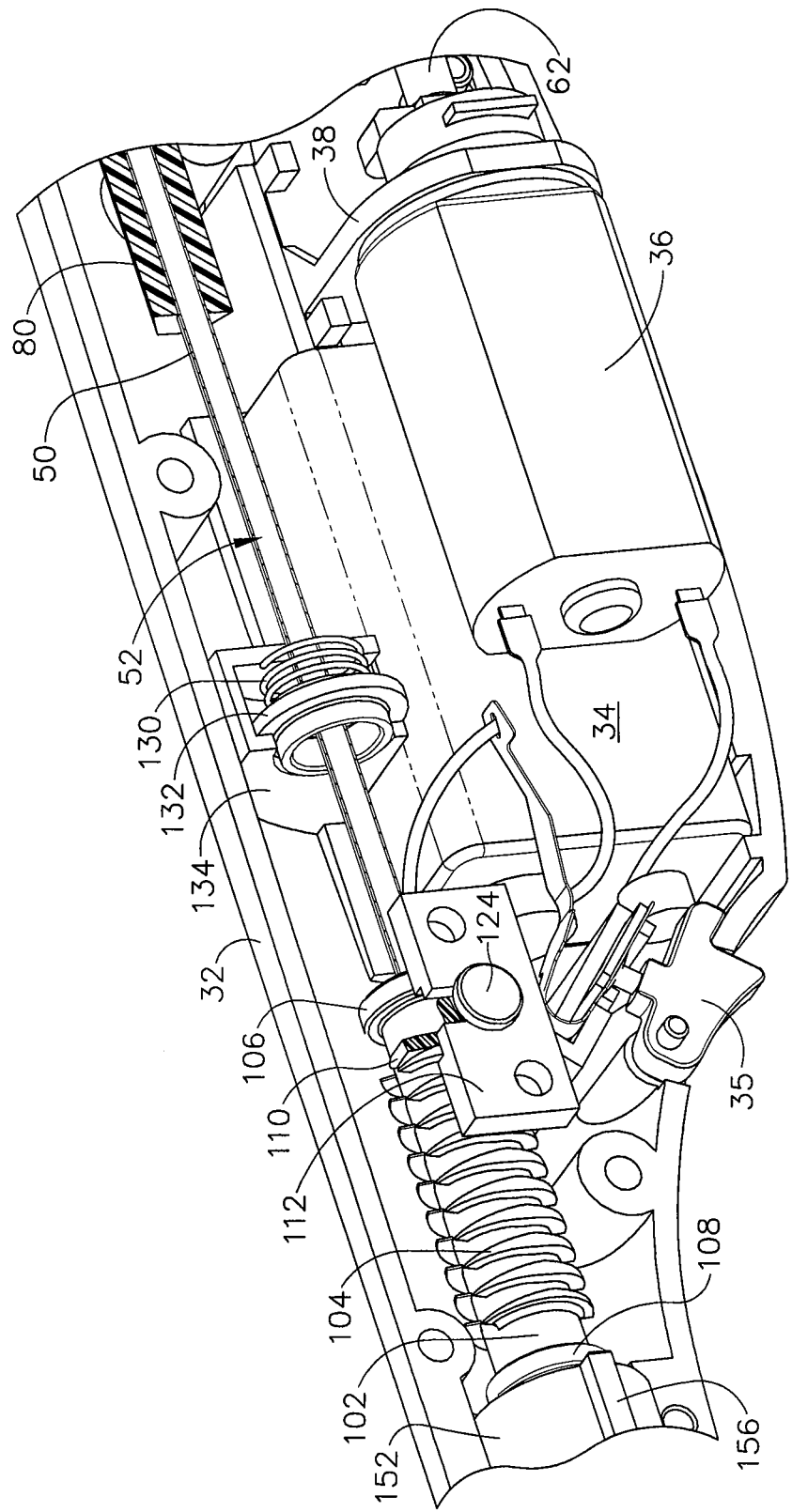
FIG. 7 depicts a partial perspective view of a central portion of the biopsy device of FIG. 1, with a housing component removed, and with a cutter overmold in cross-section.

Needle (20) of the present example further comprises a hub (200), as shown in FIGS. 2-4. Hub (200) may be formed of plastic that is overmolded about needle (20) or otherwise secured to needle (20), such that hub (200) is unitarily secured to needle (20). Alternatively, hub (200) may be formed of any other suitable material through any suitable process and may have any other suitable relationship with needle (20). Hub (200) of the present example comprises a thumbwheel (202) and a sleeve portion (204). Thumbwheel (202) is operable to rotate needle (20) about its longitudinal axis, such as to re-orient lateral aperture (24) about the longitudinal axis. Such re-orientation of lateral aperture (24) may facilitate targeted acquisition of tissue samples, such as when multiple tissue samples are taken during a single insertion of needle (20) in a patient's breast. Examples of such multi-orientation tissue sample acquisition are disclosed in U.S. Pat. No. 5,526,822, entitled "Method and Apparatus for Automated Biopsy and Collection of Soft Tissue," issued Jun. 18, 1996, the disclosure of which is incorporated by reference herein. Alternatively, the user may rotate the entire biopsy device (10) about its longitudinal axis to provide re-orientation of lateral aperture (24); or may simply refrain from re-orienting lateral aperture (24).

Sleeve portion (204) extends integrally and proximally from thumbwheel (202), into body (30). As shown in FIG. 10, sleeve portion (204) defines a hollow interior (206), which is in fluid communication with second lumen (28) of needle (20). Sleeve portion (204) also defines an opening (208), which is in fluid communication with hollow interior (206). Opening (208) is therefore in fluid communication with second lumen (28) of needle (20) in this example. As will be described in greater detail below, opening (208) is selectively exposed to ambient air during use of biopsy device (10), to selectively provide venting to second lumen (28). A pair of o-rings (210) are positioned about sleeve portion (204), on either side of opening (208), to substantially seal opening (208), interior (206), and second lumen (28) when second lumen (28) is not to be vented. A seal (212) is also provided at the proximal end of sleeve (204), at the interface of cutter (50) and sleeve (204). Seal (212) is configured to substantially seal the interface of cutter (50) and sleeve (204), even as cutter (50) rotates and translates relative to sleeve (204).

It should be understood that, as with other components described herein, needle (20) may be varied, modified, substituted, or supplemented in a variety of ways; and that needle (20) may have a variety of alternative features, components, configurations, and functionalities. By way of example only, needle (20) may simply lack second lumen (28) altogether in some versions, such that first lumen (26) is the only lumen defined by needle (20). Other suitable alternative versions, features, components, configurations, and functionalities of needle (20) will be apparent to those of ordinary skill in the art in view of the teachings herein. Similarly, other suitable modifications to other components of biopsy device (10) that may be made in accordance with variations of needle (20) (e.g., modifying or omitting valve mechanism (150) in versions where second lumen (28) is omitted from needle (20), etc.) will be apparent to those of ordinary skill in the art in view of the teachings herein.

Exemplary Body

As shown in FIGS. 1 and 3, body (30) of the present example comprises a pair of housing members (32). As shown in FIGS. 2 and 4, in which one housing member (32) has been removed, as well as the exploded view of FIG. 3, a battery (34), motor (36), and vacuum pump (38) are provided within body (30). Battery (34) may comprise a rechargeable battery, a non-rechargeable battery, or any other type of battery. In addition, battery (34) may provide nine volts or any other suitable voltage. In other versions, biopsy device (10) is powered by some other source, such as a conventional AC power source or piece of capital equipment, such that battery (34) is merely optional. Battery (34) is coupled with motor (36) via a trigger switch (35) in the present example. In particular, when trigger switch (35) is not being actuated by a user, the circuit between battery (34) and motor (36) is open, such that motor (36) is inactive; whereas the circuit between battery (34) and motor (36) is closed when a user actuates trigger switch (35), thereby activating motor (36). It should be understood that any suitable structures or components may be used to provide a trigger switch (35), and that the particular trigger switch (35) shown in FIGS. 1-4 is just one example.

As shown in FIGS. 2-4, motor (36) of the present example is in mechanical communication with vacuum pump (38) and a cutter rotation mechanism (60). In particular, motor (36) is operable to simultaneously activate vacuum pump (38) and cutter rotation mechanism (60) when motor (36) is activated. Alternatively, vacuum pump (38) and cutter rotation mechanism (60) may be activated in any other suitable fashion. By way of example only, vacuum pump (38) and/or cutter rotation mechanism (60) may be activated manually and/or by separate motors and/or in any other suitable fashion. Motor (36) of the present example comprises a conventional DC motor. However, it should be understood that motor (36) may alternatively comprise a pneumatic motor (e.g., with impeller, etc.), a pneumatic linear actuator, an electromechanical linear actuator, or a variety of other types of movement-inducing devices. Various suitable ways in which other types of movement-inducing devices may be incorporated into biopsy device (10) will be apparent to those of ordinary skill in the art in view of the teachings herein.

Vacuum pump (38) of the present example comprises a conventional diaphragm pump. In particular, a drive shaft (62), which is rotationally driven by motor (36), is coupled with an eccentric (not shown—e.g., a device for converting circular motion into rectilinear motion, comprising a disk fixed off-center to drive shaft (62), and working freely in a surrounding collar), which is configured to cause a rod (not shown—e.g., the rod may be fixed to a surrounding color of the eccentric) of vacuum pump (38) to reciprocate as motor (36) and drive shaft (62) rotate. This rod of vacuum pump (38) drives a diaphragm (not shown) of vacuum pump (38) as the rod reciprocates, causing vacuum pump (38) to induce a vacuum. Of course, any other suitable type of vacuum pump may be used. Vacuum pump (38) of the present example is operable to induce a vacuum in tissue sample holder (40) when vacuum pump (38) is activated, as will be described in greater detail below. Cutter rotation mechanism (60) is operable to rotate cutter (50) when cutter rotation mechanism (60) is activated, as will also be described in greater detail below. In particular, cutter rotation mechanism (60) is operable to cause cutter (50) to rotate within first lumen (26), while a cutter translation mechanism (100) is operable to concomitantly cause cutter (50) to translate within first lumen (26), such as to sever a biopsy sample from tissue protruding through lateral aperture (24).

It should be understood that, as with other components described herein, body (30) may be varied, modified, substituted, or supplemented in a variety of ways; and that body (30) may have a variety of alternative features, components, configurations, and functionalities. Suitable alternative versions, features, components, configurations, and functionalities of body (30) will be apparent to those of ordinary skill in the art in view of the teachings herein.

Exemplary Valve Mechanism

As shown in FIGS. 2-4 and 10, biopsy device (10) also includes a valve mechanism (150) in the present example. Valve mechanism (150) of this example comprises a barrel (152), a resilient member (154), and sleeve (204) of needle hub (200). Barrel (152) is positioned coaxially about sleeve (204) of needle hub (200), and is configured to translate relative to sleeve (204). O-rings (210) are configured to seal the exterior of sleeve portion (204) against the interior sidewall of barrel (152), even as barrel (152) translates relative to sleeve portion (204), and even as sleeve portion (204) rotates relative to barrel (152). Barrel (152) includes a pair of opposing longitudinal external ribs (156) and an annular flange (158). Ribs (156) engage housing members (32), such that ribs (156) and housing members (32) permit barrel (152) to translate within body (30) while preventing barrel (152) from rotating within body (30). Barrel (152) also defines an opening (160). Opening (160) of barrel (152) is configured to be selectively placed in fluid communication with opening (208) of sleeve portion (204), depending on the longitudinal position of barrel (152). In particular, opening (160) of barrel (152) is placed in fluid communication with opening (208) of sleeve portion (204) when barrel (152) is in a distal position; while opening (160) of barrel (152) is not in fluid communication with opening (208) of sleeve portion (204) when barrel (152) is in a proximal position. Furthermore, opening (208) of sleeve portion (204) may be further sealed off from opening (160) of barrel (152) by the proximal o-ring (210) when barrel (152) is in a proximal position, such that opening (208) is fluidly isolated from opening (160). As a mere example, FIG. 10 shows openings (160, 208) in fluid communication with each other; while FIG. 13 shows openings (160, 208) in fluid isolation relative to each other.

It should be understood from the foregoing that opening (160) of barrel (152) may be selectively placed in fluid communication with second lumen (28), based on the longitudinal position of barrel (152). In addition, as shown in FIGS. 2-4 and 10, housing members (32) define a vent opening (162), which opens to ambient air. Opening (160) of barrel (152) may also be selectively placed in fluid communication with vent opening (162) of body (30), based on the longitudinal position of barrel (152). In particular, opening (160) of barrel (152) may selectively provide a fluid coupling between opening (208) of sleeve portion (204) and vent opening (162) of body (30) when barrel (152) is in a distal position. As a mere example, FIG. 10 shows opening (160) in fluid communication with vent opening (162); while FIG. 13 shows opening (160) in fluid isolation relative to vent opening (162). It should therefore be understood from the foregoing that barrel (152) and associated components may substantially seal off second lumen (28) when barrel (152) is in a proximal position; and that barrel (152) and associated components may vent second lumen (28) to atmosphere when barrel (152) is in a distal position. As described in greater detail below, barrel (152) is in the distal position when cutter (50) is at a distal-most position; while barrel (152) is in the proximal position at other times under the bias of resilient member (154).

Resilient member (154) is positioned coaxially about barrel (152), is distally engaged by housing members (32), and is proximally engaged by flange (158) of barrel (152). Resilient member (154) is configured to bias barrel (152) proximally. In the present example, resilient member (154) comprises a coil spring, though any other suitable type of resilient member may be used (e.g., leaf springs, something other than a spring, etc.). Resilient member (154) biases barrel (152) to a proximal position, to thereby substantially seal off second lumen (28). However, resilient member (154) permits barrel (152) to be moved to a distal position, to thereby vent second lumen (28) to atmosphere, when cutter (50) reaches a distal-most position as described in greater detail below.

It should be understood that, as with other components described herein, valve mechanism (150) may be varied, modified, substituted, or supplemented in a variety of ways; and that valve mechanism (150) may have a variety of alternative features, components, configurations or functionalities. Suitable alternative versions, features, components, configurations, and functionalities of valve mechanism (150) will be apparent to those of ordinary skill in the art in view of the teachings herein.

Exemplary Tissue Sample Holder

As shown in FIGS. 1-4 and 8, tissue sample holder (40) of the present example comprises a mount (42), an outer cup (44), and a filter tray (46). Mount (42) of the present example is coupled with housing members (32), such that mount (42) is sealingly coupled with body (30). Outer cup (44) is configured to removably couple with mount (42). By way of example only, outer cup (44) may engage with mount (42) through a bayonet fitting, through complementary threads, or in any other suitable fashion. An o-ring (43) provides a seal between outer cup (44) and mount (42) in the present example, though any suitable substitute or supplement may be used for sealing. Alternatively, o-ring (43) or other type of seal may be omitted in some versions. Outer cup (44) of the present example is substantially transparent, allowing the user to view tissue samples on filter tray (46), though outer cup (44) may have any other suitable properties if desired. Filter tray (46) of the present example has a plurality of slits (47) formed therethrough. Slits (47) are sized and configured to permit the passage of fluids therethrough while preventing the passage of tissue samples therethrough. Filter tray (46) is thus configured to receive tissue samples that are communicated proximally through cutter (50) as will be described in greater detail below. It should be understood that filter tray (46) may take a variety of alternate forms. By way of example only, a plurality of round openings or other features may be formed through filter tray (46) in addition to or in lieu of slits (47). As another merely illustrative alternative, filter tray (46) may be substituted with a textile mesh and/or other structure (s) or component(s). Still other suitable components and configurations for a tissue sample holder (40) will be apparent to those of ordinary skill in the art.

As noted above, vacuum pump (38) is in fluid communication with tissue sample holder (40) in the present example. In particular, vacuum pump (38) is coupled with a conduit (39), which is coupled with a hydrophobic filter (48), which is in fluid communication with the interior space defined by outer cup (44) and mount (42). Hydrophobic filter (48) is configured to permit vacuum pump (38) to induce a vacuum in tissue sample holder (40) while preventing liquids from being communicated from tissue sample holder (40) to vacuum pump (38). In addition to or in lieu of having hydrophobic filter (48) a highly absorbent material may be provided in tissue sample holder (40) to soak up liquids. Alternatively, liquids may be dealt with in any other suitable fashion. As described in greater detail below, the vacuum created in tissue sample holder (40) by vacuum pump (38) is communicated to cutter (50) in the present example.

It should be understood that, as with other components described herein, tissue sample holder (40) may be varied, modified, substituted, or supplemented in a variety of ways; and that tissue sample holder (40) may have a variety of alternative features, components, configurations, and functionalities. For instance, tissue sample holder (40) may be alternatively configured such that it has a plurality of discrete tissue sample compartments that may be selectively indexed to cutter lumen (52). Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Non-Provisional patent application Ser. No. 12/337,997, entitled "Tissue Biopsy Device with Rotatably Linked Thumbwheel and Tissue Sample Holder," filed Dec. 18, 2008; U.S. Non-Provisional patent application Ser. No. 12/337,911, entitled "Biopsy Device with Discrete Tissue Chambers," filed Dec. 18, 2008, the disclosure of which is incorporated by reference herein; or U.S. Non-Provisional patent application Ser. No. 12/337,874, entitled "Mechanical Tissue Sample Holder Indexing Device," filed Dec. 18, 2008, the disclosure of which is incorporated by reference herein. Other suitable alternative versions, features, components, configurations, and functionalities of tissue sample holder (40) will be apparent to those of ordinary skill in the art in view of the teachings herein.

Exemplary Cutter

Figure 8:
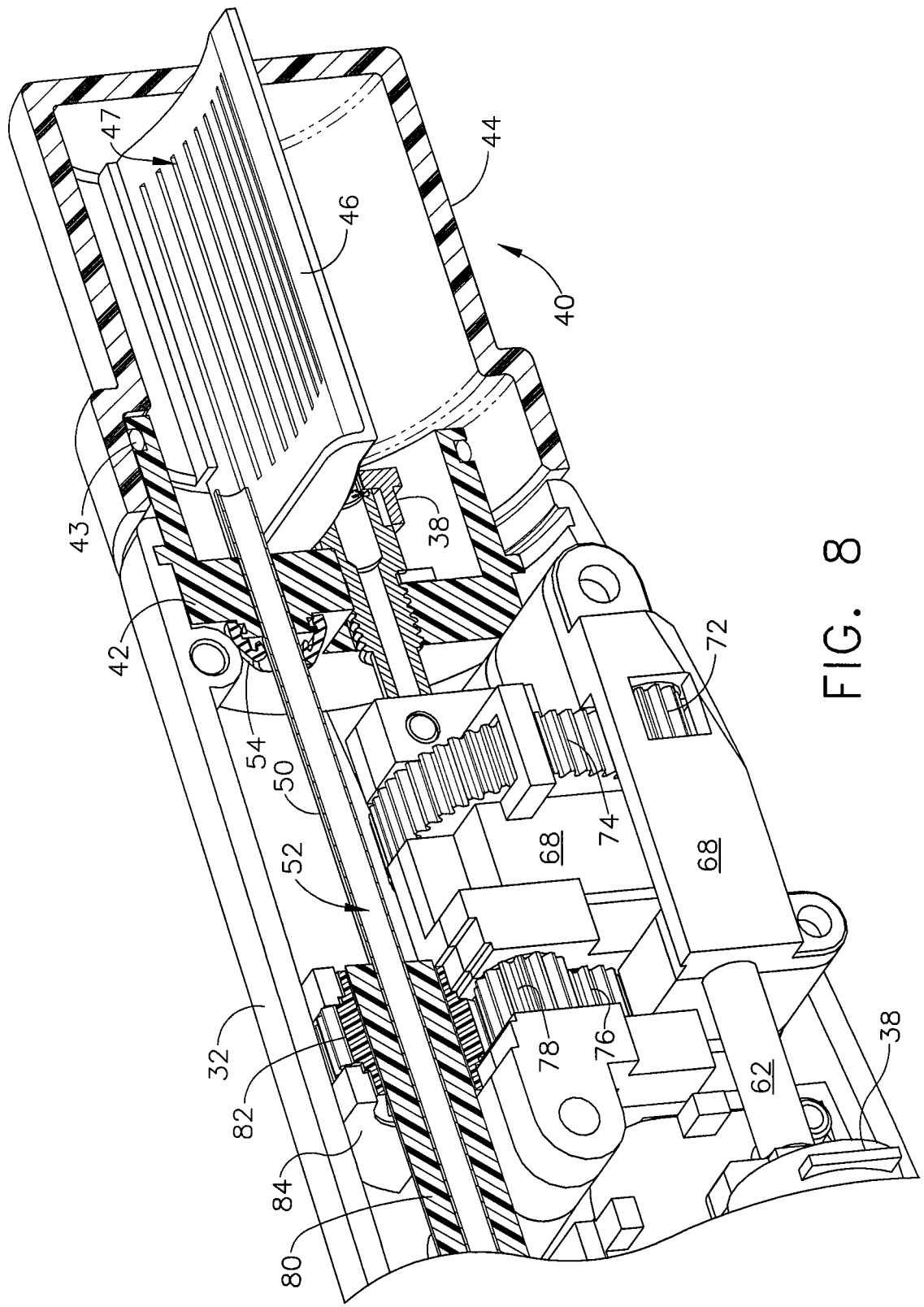
FIG. 8 depicts a partial perspective view of a proximal portion of the biopsy device of FIG. 1, with a housing component removed, and with a tissue sample holder cup in cross-section.

As shown in FIG. 5, cutter (50) of the present example is substantially hollow, such that cutter (50) defines a cutter lumen (52). As shown in FIG. 12, cutter (50) also has a substantially sharp distal edge (51), such that cutter (50) is operable to sever a biopsy sample from tissue protruding through lateral aperture (24) of needle (20). In particular, sharp distal edge (51) of the present example extends along a portion of the length of cutter (50) and about the circumferential perimeter at the distal end of cutter (50), thus providing a scoop-like shape at the distal end of cutter (50). In other versions, there is no longitudinal component to distal edge (51) and the distal end of cutter (50) is substantially tubular, such that distal edge (51) simply extends about the full circumference of cutter (50) without having any longitudinal component. Alternatively, the distal end of cutter (50) may have any other suitable configuration. As shown in FIGS. 2, 4, and 8, a proximal portion of cutter (50) extends into tissue sample holder (40). A vacuum created in tissue sample holder (40) by vacuum pump (38) is thus communicated to cutter lumen (52). A seal (54) is provided at the interface of cutter (50) and mount (42). Seal (54) is configured to substantially seal the interface of cutter (50) and mount (42), even as cutter (50) rotates and translates relative to mount (42). Furthermore, cutter (50) is configured such that it remains in sealed fluid communication with the interior of tissue sample holder

(40) even when cutter (50) is in a distal most position. For instance, the length of cutter (50) may be such that at least a portion of cutter (50) is always disposed in mount (42) of tissue sample holder (40) during operation of biopsy device (10). Of course, cutter (50) may have any other suitable alternative features or configurations. Similarly, cutter (50) may have any other suitable alternative relationships with tissue sample holder (40).

It should be understood that, as with other components described herein, cutter (50) may be varied, modified, substituted, or supplemented in a variety of ways; and that cutter (50) may have a variety of alternative features, components, configurations, and functionalities. Suitable alternative versions, features, components, configurations, and functionalities of cutter (50) will be apparent to those of ordinary skill in the art in view of the teachings herein.

Exemplary Cutter Rotation Mechanism

Figure 25:
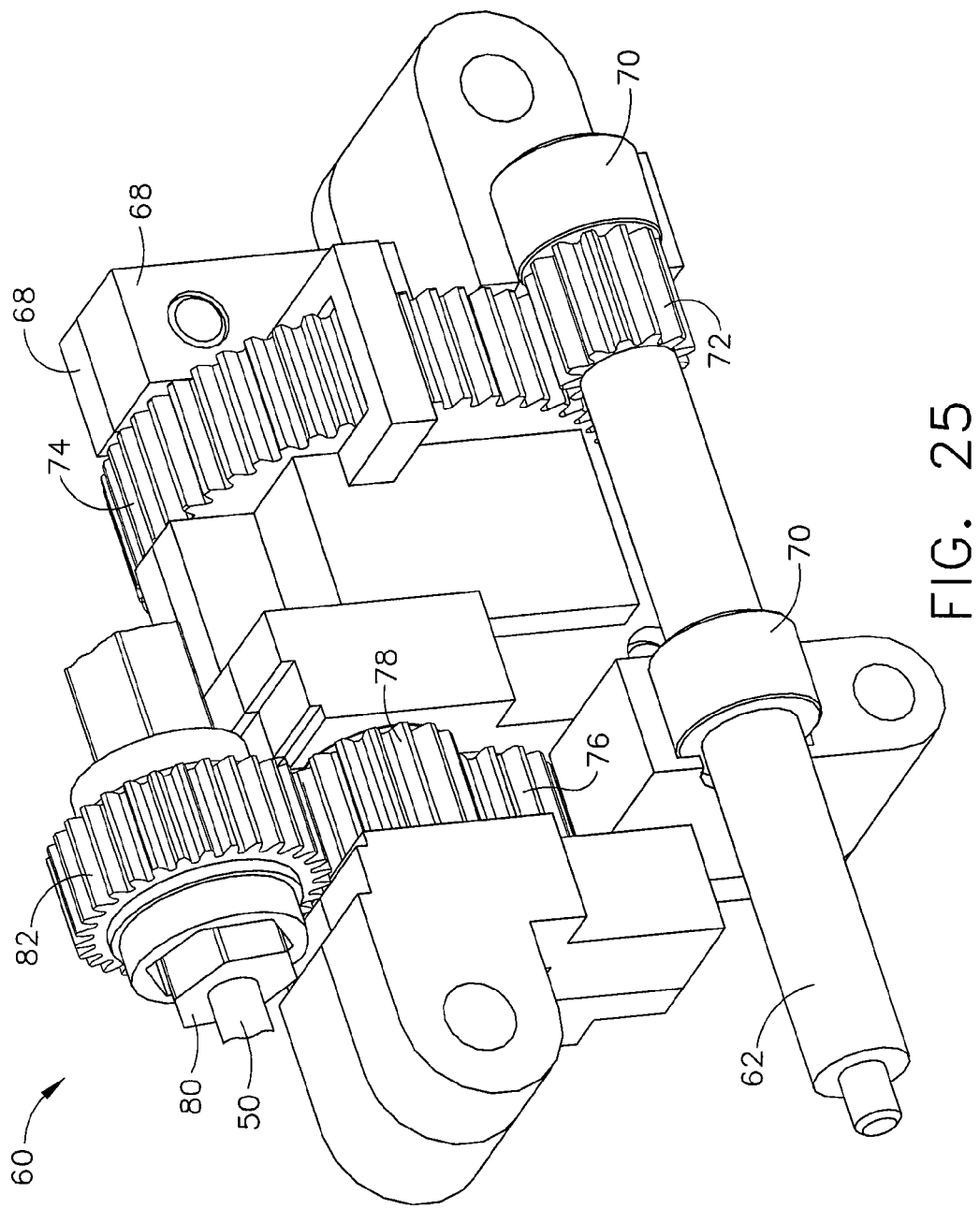
FIG. 25 depicts a perspective view of the cutter rotation mechanism of the biopsy device of FIG. 1.
Figure 26:
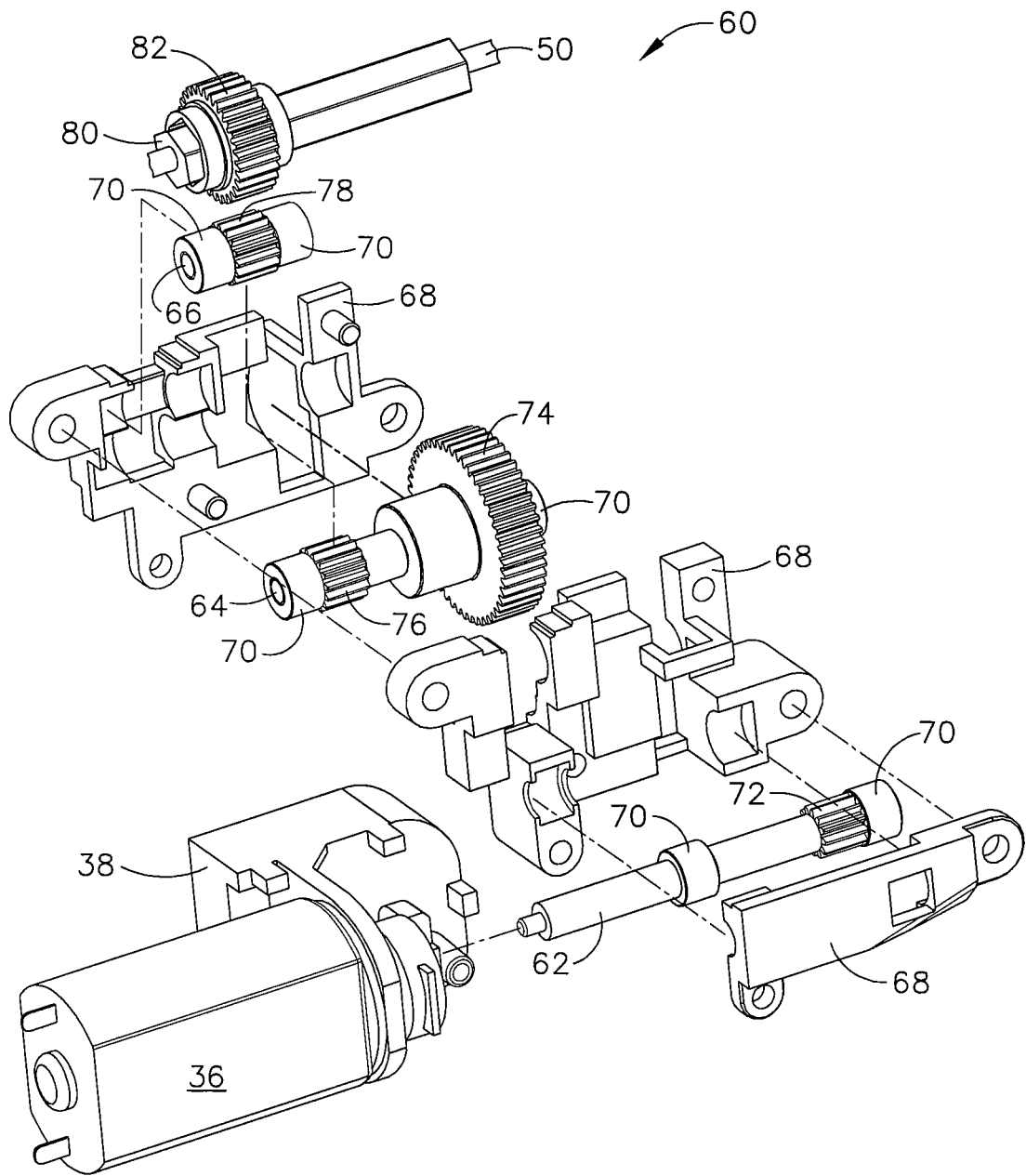
FIG. 26 depicts an exploded perspective view of the cutter rotation mechanism of FIG. 25.

As shown in FIGS. 2-4, 8, and 25-26, cutter rotation mechanism (60) of the present example comprises a first shaft (62), a second shaft (64), a third shaft (66), and housing components (68). Each shaft (62, 64, 66) has a pair of associated bearings (70), which provide engagement between shafts (62, 64, 66) and housing components (68) while permitting shafts (62, 64, 66) to rotate freely relative to housing components (68). Any suitable structures may be used for bearings (70); or bearings (70) may be omitted if desired. First shaft (62) extends from motor (36), such that motor (36) is configured to rotatingly drive first shaft (62). First shaft (62) also has a drive gear (72), which rotates unitarily with first shaft (62). Second shaft (64) has a driven gear (74) and a drive gear (76), each of which rotates unitarily with second shaft (64). Third shaft (66) also has a gear (78), which rotates unitarily with third shaft (66). As shown in FIGS. 25-26, drive gear (72) of first shaft (62) meshes with driven gear (74) of second shaft (64); while drive gear (76) of second shaft (64) meshes with gear (78) of third shaft (66). Accordingly, gear (78) rotates when motor (36) is activated in this example.

As shown in FIGS. 2-4 and 8, cutter rotation mechanism (60) of the present example further comprises a sleeve (80) that is unitarily secured to cutter (50); and a nut (82) that is configured to fit over sleeve (80). In particular, sleeve (80) of this example is hexagonal shaped, presenting six flat faces; while nut (82) defines a hexagonal opening with six flat faces that are configured to complement the flat faces of sleeve (80). The engagement between sleeve (80) and nut (82) is therefore such that rotation of nut (82) provides corresponding rotation of sleeve (80). The engagement between sleeve (80) and nut (82) is also such that nut (82) may slide longitudinally relative to sleeve (80), even as nut (82) and sleeve (80) simultaneously rotate. For instance, the longitudinal position of nut (82) may stay substantially constant as cutter (50) and sleeve (80) translate longitudinally. Bosses (84) are formed in housing members (32) in the present example to maintain the longitudinal position of nut (82), while also permitting nut (82) to rotate. Furthermore, in the present example, sleeve (80) is overmolded about cutter (50), such that cutter (50) and sleeve (80) rotate and translate unitarily. For instance, sleeve (80) may be formed of a plastic material that is overmolded about a metal cutter (50). Alternatively, any other suitable materials and methods of forming may be used for sleeve (80) and cutter (50), and sleeve (80) may be secured to cutter (50) in any other suitable fashion (e.g., using set screw, bonding, etc.). It should also be understood that sleeve (80) and nut (82) may have a variety of other configurations (e.g., complementary key and keyway instead of hex features, etc.) and relationships. Similarly, a variety of other structures or components may be used in addition to or in lieu of sleeve (80) and/or nut (82).

In the present example, the exterior of nut (82) is configured to mesh with gear (78), such that rotation of gear (78) causes rotation of nut (82). Such rotation of nut (82) will cause corresponding rotation of cutter (50) as noted above. It will therefore be understood that cutter rotation mechanism (60) may cause rotation of cutter (50) in response to activation of motor (36), with rotation of motor (36) being communicated to cutter (50) through shafts (62, 64, 66), gears (72, 74, 76, 78), nut (82), and sleeve (80). Cutter rotation mechanism (60) of the present example provides an 8:1 gearing ratio, though it should be understood that any other suitable gearing ratio may be provided (e.g., 10:1 or some other gearing ratio). Of course, any other suitable structures, components, configurations, or techniques may be used to provide rotation of cutter (50). It should therefore be understood that, as with other components described herein, cutter rotation mechanism (60) may be varied, modified, substituted, or supplemented in a variety of ways; and that cutter rotation mechanism (60) may have a variety of alternative features, components, configurations, and functionalities. Suitable alternative versions, features, components, configurations, and functionalities of cutter rotation mechanism (60) will be apparent to those of ordinary skill in the art in view of the teachings herein. Alternatively, biopsy device (10) may be configured such that cutter (50) does not rotate.

Exemplary Cutter Translation Mechanism

Figure 11:
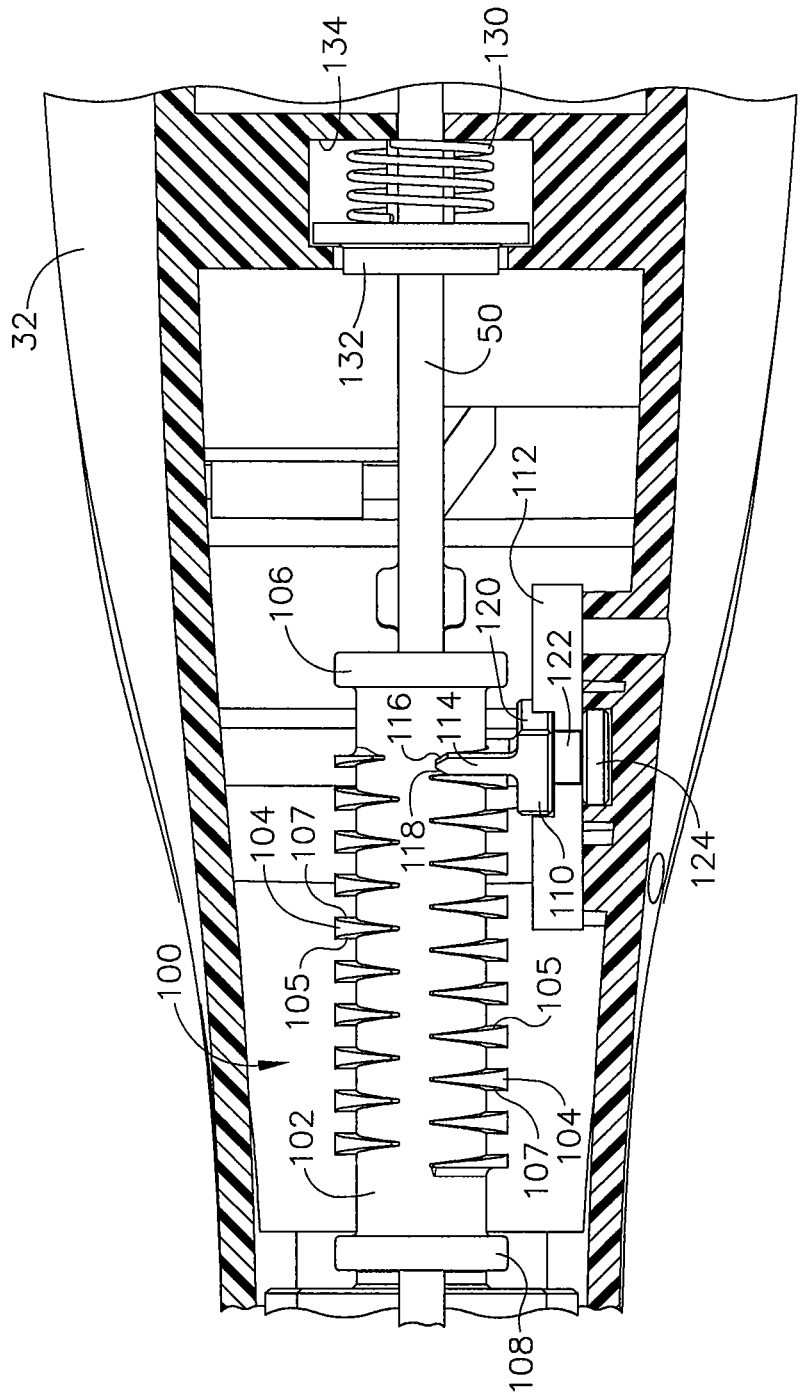
FIG. 11 depicts a top plan view of the cutter translation mechanism of the biopsy device of FIG. 1, with part of the biopsy device housing in cross-section, and with the cutter at the starting position of FIG. 9.

Biopsy device (10) of the present example further includes a cutter translation mechanism (100), which is responsive to rotation of cutter (50). In particular, and as shown in FIGS. 2-4, 7, and 11-24, cutter translation mechanism (100) of the present example comprises a lead screw (102), a rocking pawl (110), and a pawl mount (112). Lead screw (102) comprises a set of diamond-shaped two-way threads (104), a proximal flange (106), and a distal flange (108). Lead screw (102) is overmolded about cutter (50) in the present example, such that cutter (50) and lead screw (102) rotate and translate unitarily. For instance, lead screw (102) may be formed of a plastic material that is overmolded about a metal cutter (50). Alternatively, any other suitable materials and methods of forming may be used for lead screw (102) and cutter (50), and lead screw (102) may be secured to cutter (50) in any other suitable fashion (e.g., using set screw, bonding, etc.). As shown in FIGS. 4 and 11, two-way threads (104) are discrete from each other, and each thread (104) presents a pair of cutter retraction camming faces (105) and a pair of cutter advancement camming faces (107). As will be described in greater detail below, camming faces (105, 107) of threads (104) provide two-way translation of lead screw (102) in response to unidirectional rotation of lead screw (102), depending on the orientation of rocking pawl (110). Each thread (104) does not extend around the full circumference of lead screw (102) in the present example, which allows pawl (110) to cross from one thread to another regardless of whether pawl (110) is in a forward orientation or a rearward orientation, which thereby provides the self-reversing capability of cutter translation mechanism (100) of this example.

Figure 27:
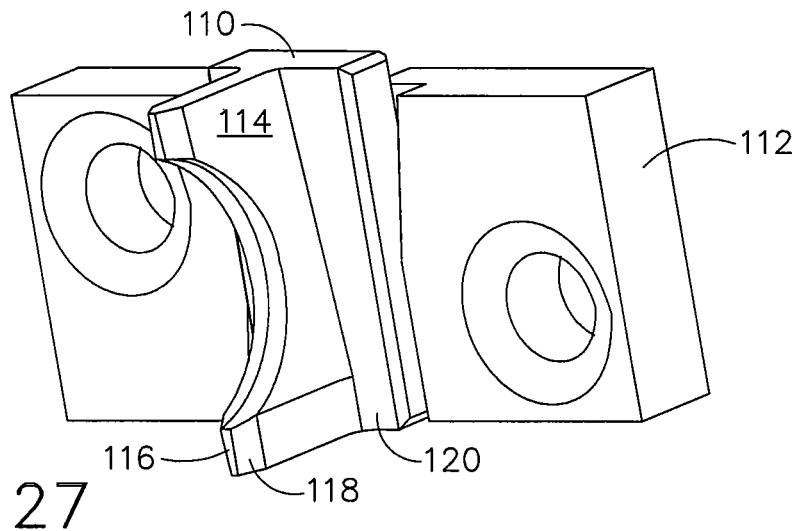
FIG. 27 depicts a perspective view of the rocking pawl assembly of the cutter translation mechanism of FIG. 11.
Figure 28:
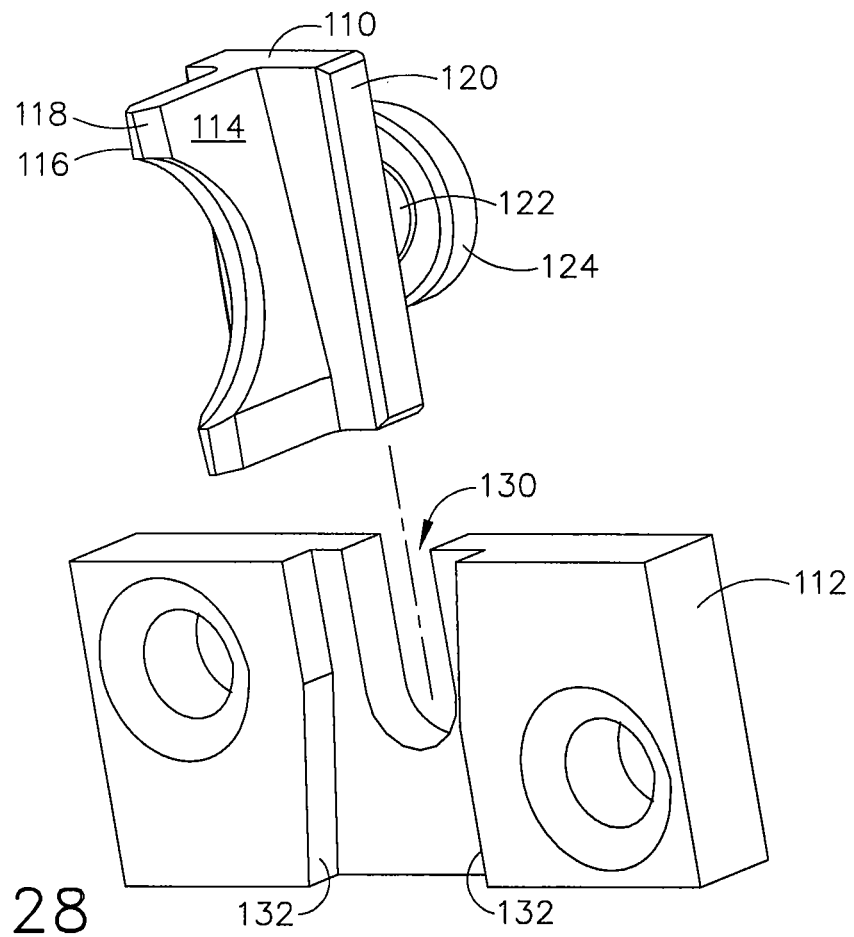
FIG. 28 depicts an exploded perspective view of the rocking pawl assembly of FIG. 27.

As best shown in FIGS. 27-28, rocking pawl (110) is slidingly engaged with pawl mount (112) in the present example. Pawl (110) comprises a projection (114) presenting a pair of camming faces (116, 118), a first flange (120), a stem (122), and a second flange (124). Pawl mount (112) presents a slot (130) that is configured to receive stem (122) of pawl (110). In particular, slot (130) is configured to permit pawl (110) to rock or rotate relative to pawl mount (112), while flanges (120, 124) retain pawl (110) in slot (130). Pawl mount (112) also comprises a pair of engagement faces (132), which are configured to provide a degree of clearance for first flange (120) to permit pawl (110) to rock relative to pawl mount (112). Engagement faces (132) together present an hourglass-like configuration, though any other suitable configuration may be used. While permitting some rocking of pawl (110), engagement faces (132) also restrict the degree to which pawl (110) may rock in either direction. A pawl locking feature is also provided in body (30) in the present example, and is configured to engage pawl (110) and/or pawl mount (112), to secure pawl (110) and pawl mount (112) to housing member (32). It should therefore be understood that pawl (110) is permitted to rotate or rock in a limited fashion; while pawl (110) is prevented from translating.

As will be described in greater detail below, camming faces (116, 118) of pawl (110) are configured to engage camming faces (105, 107) of lead screw (102), to provide bi-directional translation of lead screw (102) based on the orientation of pawl (110) as cutter (50) rotates. In particular, engagement between camming faces (116, 118) of pawl (110) and cutter retraction camming faces (105) of threads (104) provides proximal translation of cutter (50) when cutter (50) rotates in a counterclockwise direction (viewed from tissue sample holder (40) toward needle (20)) and when pawl (110) is at a forward orientation; while engagement between camming faces (116, 118) of pawl (110) and cutter advancement camming faces (107) of threads (104) provides distal translation of cutter (50) when cutter (50) rotates in a counterclockwise direction (viewed from tissue sample holder (40) toward needle (20)) and when pawl (110) is at a rearward orientation.

Figure 14:
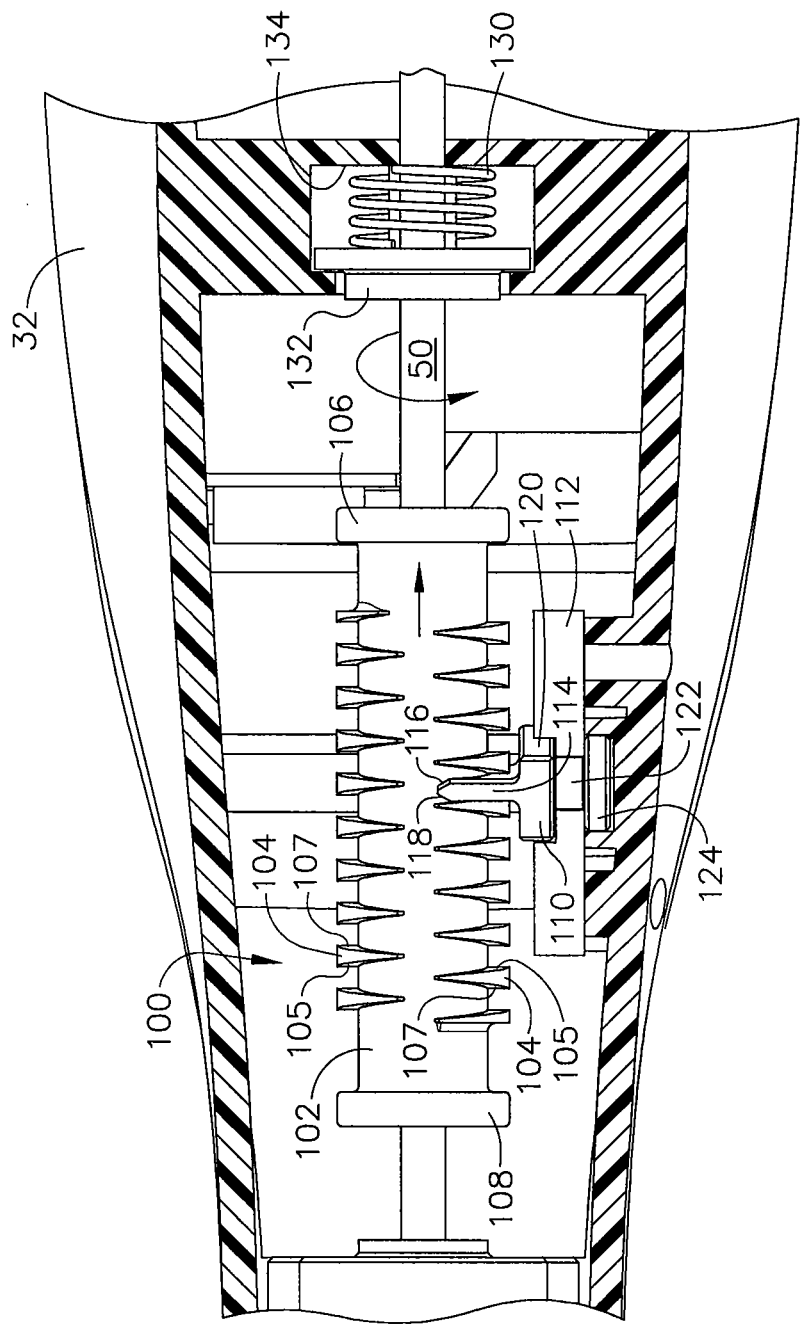
FIG. 14 depicts a top plan view of the cutter translation mechanism of FIG. 11, with part of the biopsy device housing in cross-section, and with the cutter at the intermediate position of FIG. 12, as the cutter is being retracted.
Figure 17:
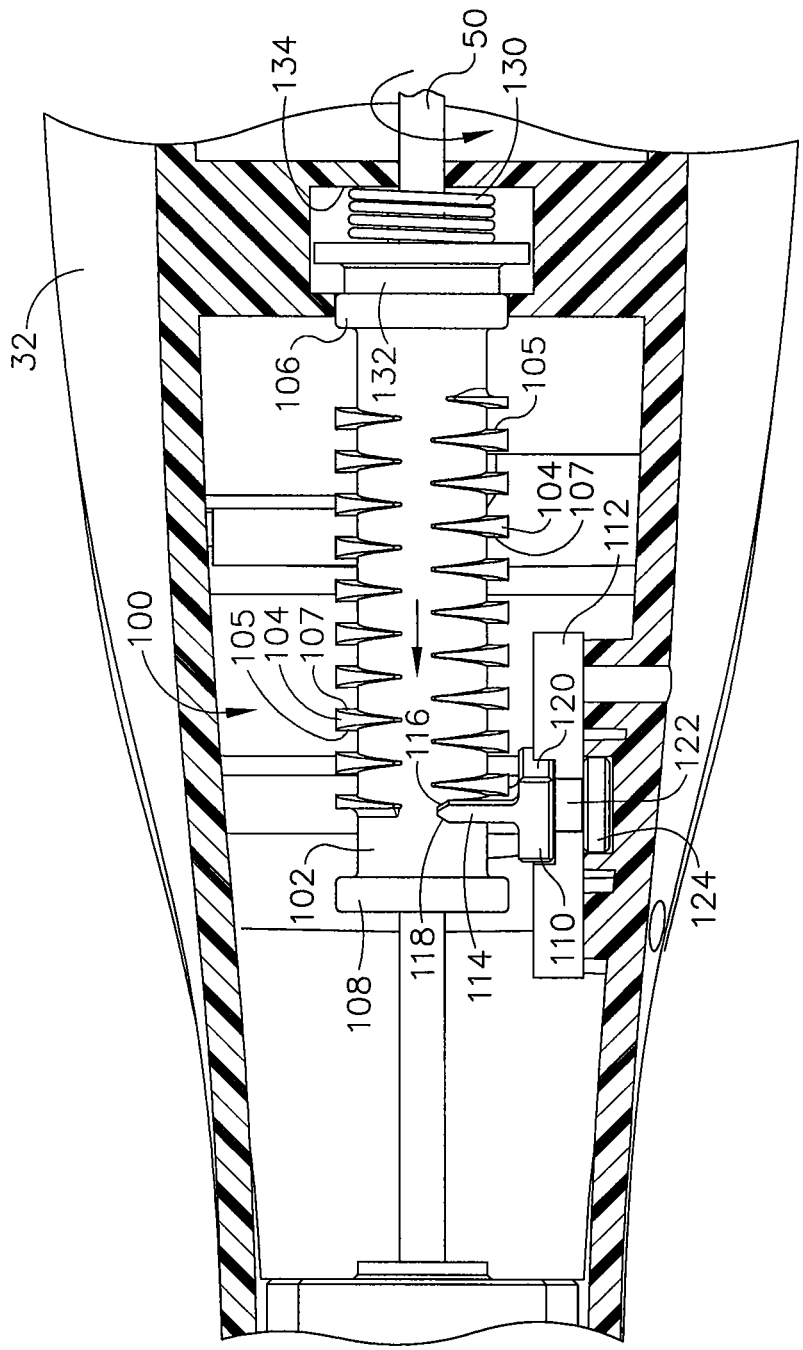
FIG. 17 depicts a top plan view of the cutter translation mechanism of FIG. 11, with part of the biopsy device housing in cross-section, and with the cutter at the retracted position of FIG. 15.
Figure 18:
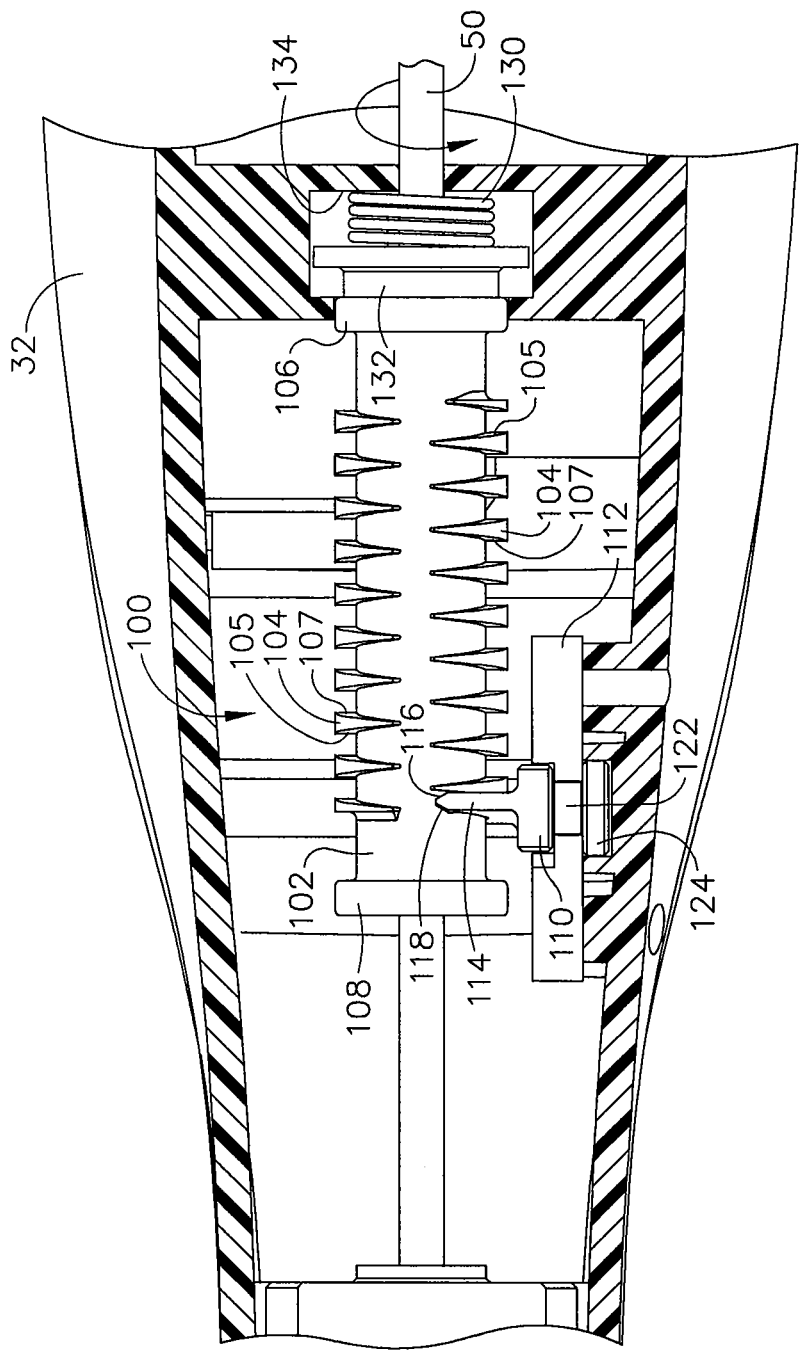
FIG. 18 depicts a top plan view of the cutter translation mechanism of FIG. 11, with part of the biopsy device housing in cross-section, and with the cutter at the retracted position of FIG. 15, with the cutter translation mechanism having self-reversed.

In one merely illustrative example of operation of cutter translation mechanism (100), cutter (50) may be initially located in a distal-most position, such that lateral aperture (24) is "closed" as shown in FIG. 9; with pawl (110) being rocked to a forward orientation, as shown in FIGS. 10-11. As cutter (50) is rotated by motor (36) and cutter rotation mechanism (60) in the counterclockwise direction, cutter translation mechanism (100) causes cutter (50) to retract proximally, as shown in FIGS. 12-14. As noted above, such proximal or rearward translation may be effected through engagement of pawl (110) with cutter retraction camming faces (105) of threads (104). As cutter (50) reaches a proximal-most position, such that lateral aperture (24) is "opened" as shown in FIG. 15, and pawl (110) may still initially still be in the forward orientation, as shown in FIGS. 16-17. However, in the present example, the orientation of pawl (110) is reversed to a rearward orientation, as shown in FIG. 18, when cutter (50) finally reaches the proximal-most position.

Such reversal of the orientation of pawl (110) when cutter (50) reaches a proximal-most position may be provided in part by resilient member (130) and disk member (132). In particular, and as shown in FIGS. 2-4, 7, and 10-11, resilient member (130) and disk member (132) are positioned between bosses (134), which are defined by housing members (32). Resilient member (130) is configured to bias disk member (132) distally, while bosses (134) are configured to retain resilient member (130) and disk member (132). In the present example, resilient member (130) comprises a coil spring, though any other suitable type of resilient member may be used (e.g., leaf springs, something other than a spring, etc.). Disk member (132) is configured to be engaged by proximal flange (106) of lead screw (102) when cutter (50) reaches a proximal-most position. Compare FIGS. 11 and 14 with FIGS. 17-18. With such engagement of proximal flange (106) and disk member (132), resilient member (130) may provide a forward or distal bias to lead screw (102). Such a forward or distal bias of lead screw (102) may suffice to cause a distal thread (104) of lead screw (102) to rock or rotate pawl (110) rearward, as shown in the transition depicted through FIGS. 17-18.

Figures 19, 20:
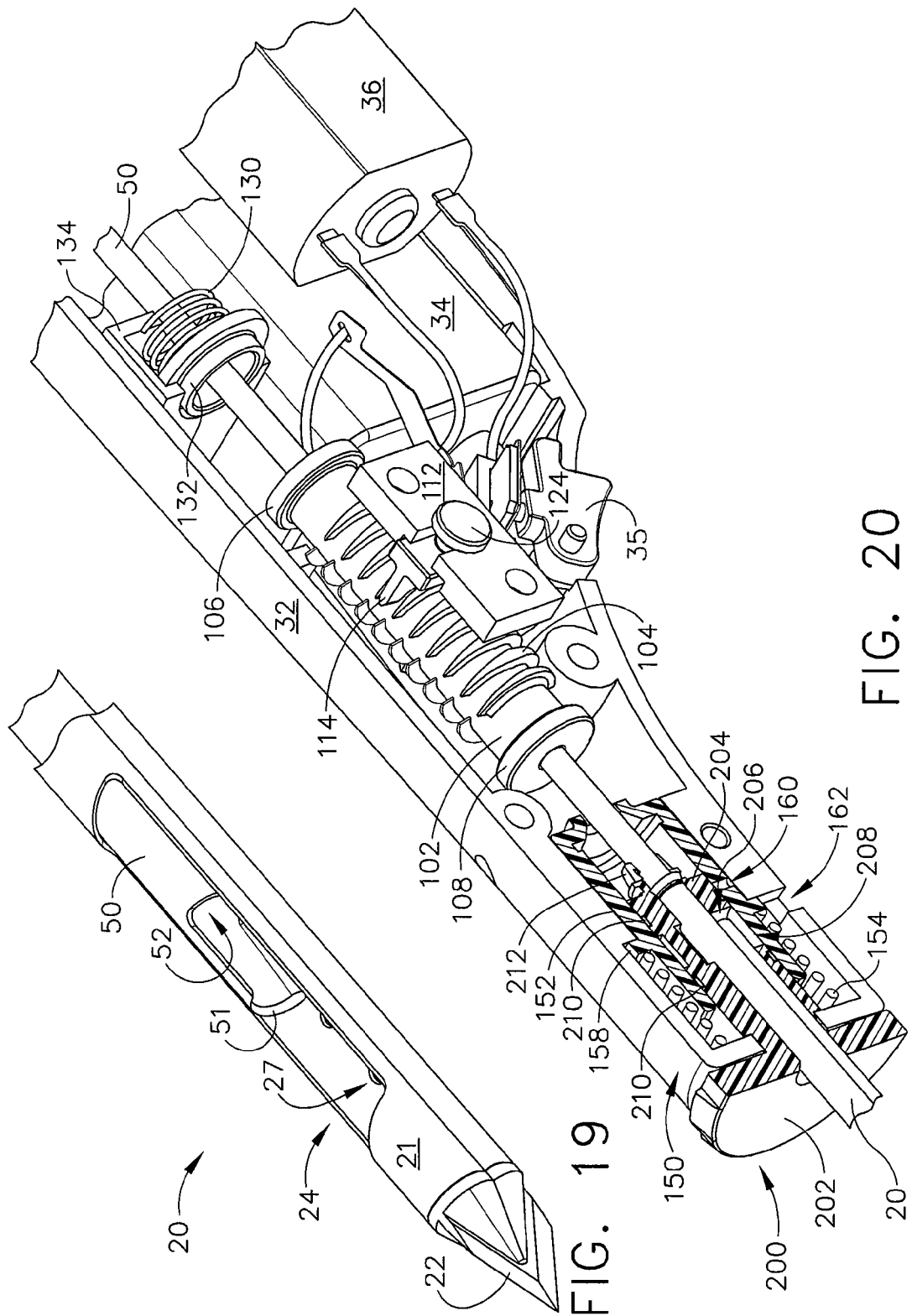
FIG. 19 depicts a partial view of the needle of the biopsy device of FIG. 1, with the cutter in an intermediate position between a distal starting position and a proximal retracted position, as the cutter is being advanced.
FIG. 20 depicts a partial side view of a central portion of the biopsy device of FIG. 1, with a housing component removed, with a valve assembly shown in cross-section, and with the cutter at the intermediate position of FIG. 19, as the cutter is being advanced.
Figure 21:
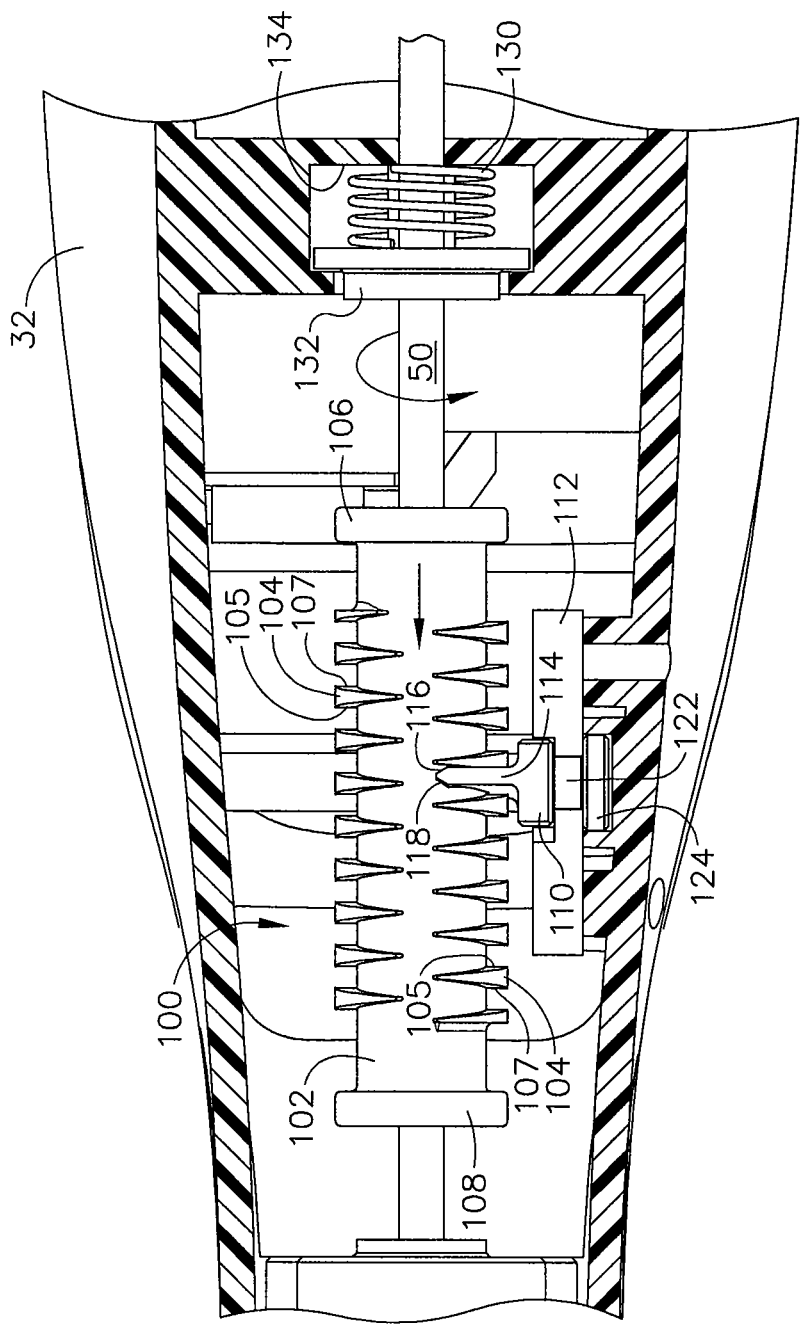
FIG. 21 depicts a top plan view of the cutter translation mechanism of FIG. 11, with part of the biopsy device housing in cross-section, and with the cutter at the intermediate position of FIG. 19, as the cutter is being advanced.
Figure 24:
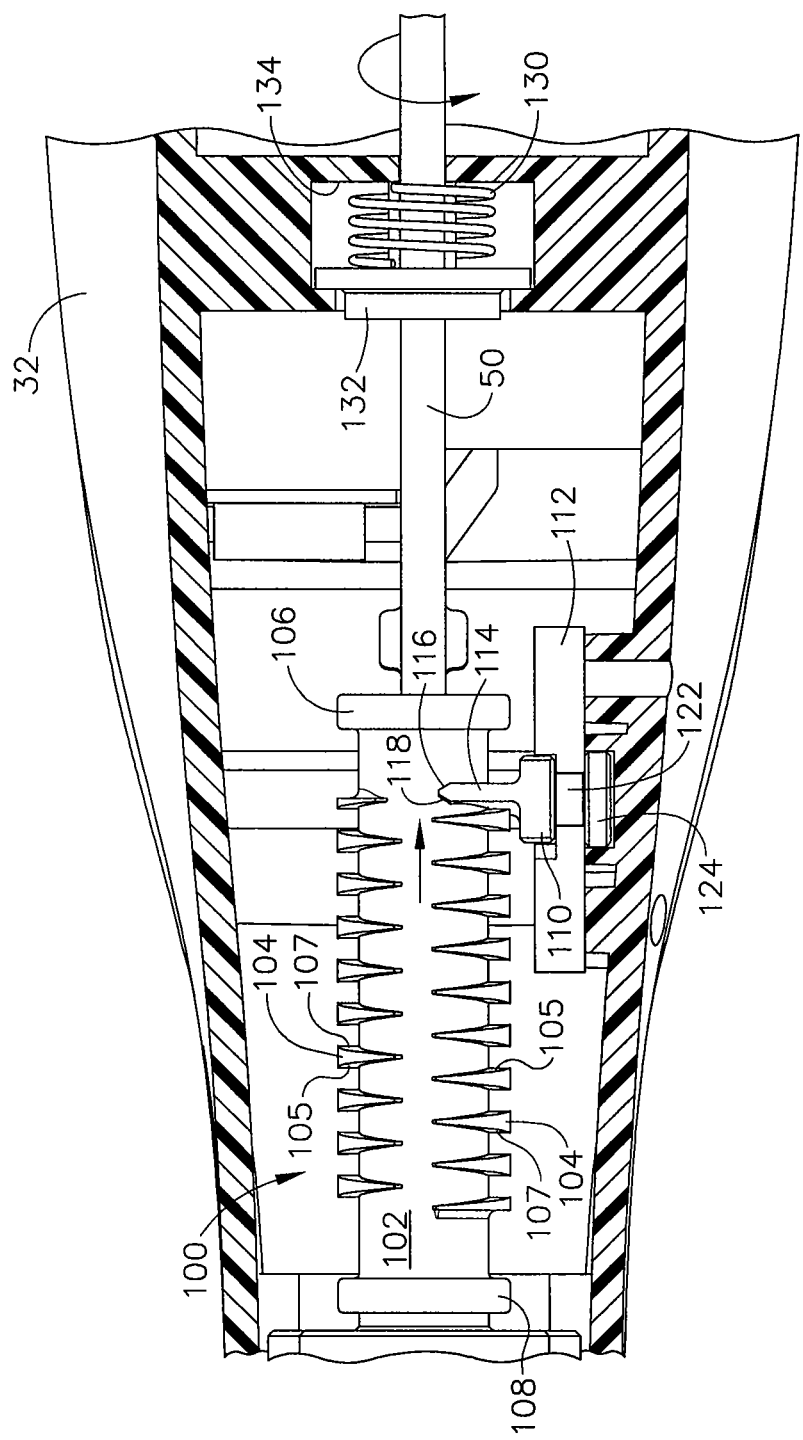
FIG. 24 depicts a top plan view of the cutter translation mechanism of the biopsy device of FIG. 11, with part of the biopsy device housing in cross-section, and with the cutter at the advanced position of FIG. 22.

With pawl (110) rocked to a rearward orientation after cutter (50) has reached the proximal-most position, and as shown in FIGS. 19-21, subsequent counterclockwise rotation of cutter (50) will cause cutter (50) to advance distally in the present example. In particular, engagement between pawl (110) and cutter advancement camming faces (107) of threads (104) causes cutter (50) to advance forward or distally as cutter (50) is rotated. As described in greater detail below, just before cutter (50) reaches a distal-most position, valve mechanism (150) "opens" second lumen (28) to atmosphere, which allows for the most recently cut tissue sample to develop a higher pressure on the distal face of the sample, with a lower pressure (negative of vacuum pressure) on the proximal face of the sample, which propels it to tissue sample holder (40). When cutter (50) again reaches a distal-most position, as shown in FIGS. 22-24, the orientation of pawl (110) may again be reversed back to the forward orientation (such that pawl (110) will engage cutter retraction camming faces (105) of threads (104)). Such reversal of the orientation of pawl (110) when cutter (50) reaches the distal-most position (e.g., at the completion of a tissue cutting stroke) may be provided in part by a valve mechanism (150). In particular, valve mechanism (150) may provide a proximal bias to lead screw (102) when cutter (50) reaches a distal-most position, to cause pawl (110) to rock or rotate back to the forward orientation as described below.

As shown in FIG. 23, the proximal face of barrel (152) is configured to be engaged by distal flange (108) of lead screw (102) when cutter (50) reaches the distal-most position. With such engagement of distal flange (108) and barrel (152), resilient member (154) may provide a proximal or rearward bias to lead screw (102). Such a proximal or rearward bias of lead screw (102) may suffice to cause a proximal thread (104) of lead screw (102) to rock pawl (110) forward back to the orientation shown in FIG. 11. If desired, another cutting stroke may be initiated by repeating the above steps.

It should be understood in view of the foregoing that cutter translation mechanism (100) of the present example is operable such that cutter (50) is translated proximally and distally in response to rotation of cutter (50) in just one rotational direction. In other words, cutter (50) may always rotate in just one rotational direction during all stages of a cutting stroke. While cutter (50) is shown and described above as rotating counterclockwise during stages of a cutting stroke, it should be immediately apparent to those of ordinary skill in the art that cutter (50) may be rotated clockwise instead during all stages of a cutting stroke. In other words, cutter translation mechanism (100) may alternatively be operated such that cutter (50) is rotated clockwise (viewed from tissue sample holder (40) toward needle (20)) to provide both proximal and distal translation of cutter (50). For instance, in versions where cutter (50) is rotated clockwise to provide both proximal and distal translation of cutter (50), pawl (110) may be at a rearward orientation to provide proximal translation of cutter (50) when cutter (50) is rotated clockwise; while pawl (110) may be at a forward orientation to provide distal translation of cutter (50) when cutter (50) is rotated clockwise. Of course, any other suitable structures, components, configurations, or techniques may be used to provide translation of cutter (50). It should therefore be understood that, as with other components described herein, cutter translation mechanism (100) may be varied, modified, substituted, or supplemented in a variety of ways; and that cutter translation mechanism (100) may have a variety of alternative features, components, configurations, and functionalities. Suitable alternative versions, features, components, configurations, and functionalities of cutter translation mechanism (100) will be apparent to those of ordinary skill in the art in view of the teachings herein. Alternatively, biopsy device (10) may be configured such that cutter (50) does not translate.

Exemplary Pneumatic Operation

As noted above, vacuum pump (38) is operable to induce a vacuum in tissue sample holder (40), and such vacuum may be further communicated to cutter lumen (52). In particular, vacuum pump (38) may start building a vacuum in cutter lumen (52) as soon as motor (36) is activated; and such a vacuum may continue to build or be maintained as cutter (50) starts moving proximally toward the retraced position. As cutter (50) moves toward retracted position, such that lateral aperture (24) of needle (20) is "partially open" as shown in FIG. 12, a vacuum in cutter lumen (52) may be further communicated through first lumen (26), which may draw tissue into lateral aperture (24). When cutter (50) reaches the retracted position, such that lateral aperture (24) of needle (20) is "open" as shown in FIG. 15, a vacuum in cutter lumen (52) may continue to be further communicated through first lumen (26), which may continue to draw tissue into lateral aperture (24). Of course, some amount of tissue may naturally prolapse into lateral aperture (24) without the assistance of vacuum, such that vacuum may not even be needed to draw tissue into lateral aperture (24). At this stage, second lumen (28) may be substantially sealed. In particular, and as shown in FIG. 16, barrel (152) of valve mechanism (150) is at the proximal position, such that barrel (152) blocks fluid communication between opening (208) of sleeve portion (204) and vent opening (162) of body (30). As cutter (50) is advanced to sever tissue protruding through lateral aperture (24), as shown in FIG. 19, vacuum pump (38) may continue to induce a vacuum in cutter lumen (52), and second lumen (28) may continue to be substantially sealed by barrel (152), as shown in FIG. 20. As cutter (50) reaches the distal-most position, as shown in FIG. 22, cutter (50) may completely sever the tissue protruding through lateral aperture (24), and distal flange (108) of lead screw (102) may simultaneously move barrel (152) distally, as shown in FIG. 23. Such distal movement of barrel (152) may vent second lumen (28) to atmosphere. Such venting may be further communicated to first lumen (28) of needle (20) via openings (27). With the severed tissue sample residing in cutter lumen (52), with vacuum pump (38) drawing a vacuum at the proximal face of the severed tissue sample, and with the venting being provided at the distal face of the severed tissue sample, the pressure differential applied to the severed tissue sample may cause the severed tissue sample to be drawn proximally through cutter lumen (52) and into tissue sample holder (40). The severed tissue sample may thus be deposited on filter tray (46) of tissue sample holder (40).

Of course, any other suitable structures, components, configurations, or techniques may be used to provide selective sealing and/or venting of second lumen (28). Furthermore, in some variations of biopsy device (10), a vacuum, saline, pressurized air, and/or any other medium may be communicated to second lumen (28) at any suitable stage of operation of biopsy device (10). Suitable alternative structures, components, configurations, or techniques for communicating severed tissue samples proximally through cutter lumen (52) to reach tissue sample holder (40) will be apparent to those of ordinary skill in the art in view of the teachings herein.

Exemplary Method of Operation

In a merely exemplary use of biopsy device (10), a user first inserts tissue piercing tip (22) into the breast of a patient. During such insertion, cutter (50) may be advanced to the distal-most position, such that lateral aperture (24) of needle (20) is closed as shown in FIGS. 9-11. As also noted herein, such insertion may be performed under stereotactic guidance, ultrasound guidance, MRI guidance, PEM guidance, BSGI guidance, palpatory guidance, some other type of guidance, or otherwise. With needle (20) sufficiently inserted into the patient's breast, the user may then activate trigger (35). Activation of trigger (35) may activate motor (36), which may in turn activate vacuum pump (38), cutter rotation mechanism (60), and cutter translation mechanism (100). Such activation of vacuum pump (38) may induce a vacuum in tissue sample holder (40) and cutter lumen (52) as described above. Such activation of cutter rotation mechanism (60) may cause cutter (50) to rotate. Such rotation of cutter (50) may cause cutter translation mechanism (100) to retract cutter (50) proximally, as shown in FIGS. 12-14. As cutter (50) starts retracting and when cutter (50) reaches the retracted position, vacuum from vacuum pump (38) (as communicated through tissue sample holder (40) and cutter lumen (52)) may draw tissue into lateral aperture (24) of needle (20). During this time, second lumen (28) may be substantially sealed by valve mechanism (150). The user may be holding trigger (35) down as cutter (50) retracts. Alternatively, a control module may be provided that keeps motor (36) activated, such that the user only needs to tap or briefly depress trigger (35).

Once cutter (50) reaches a proximal-most position, as shown in FIGS. 15-17, vacuum may still be communicated through vacuum lumen (52) and first lumen (26), drawing tissue into lateral aperture (24) of needle (20). Second lumen (28) is still substantially sealed by valve assembly (150) at this time, as shown in FIG. 16. In addition, cam (110) is rocked from a forward orientation to a rearward orientation, as shown in the transition depicted through FIGS. 17-18 as cutter (50) continues to rotate. With cam (110) being rocked, cutter (50) begins to advance distally, as shown in FIGS. 19-21. As cutter (50) advances distally, vacuum is still being communicated through vacuum lumen (52), helping to hold tissue in place as sharp distal edge (51) of cutter (50) begins to sever the tissue. Second lumen (28) is still substantially sealed by valve assembly (150) at this time, as shown in FIG. 20. Cutter (50) then reaches the distal-most position, as shown in FIGS. 22-24, thereby "closing" lateral aperture (24), and such that sharp distal edge (51) of cutter (50) completely severs the tissue. Vacuum is still being communicated through cutter lumen (52) at this time, and valve assembly (150) vents second lumen (28) through vent opening (162) as shown in FIG. 23. As described above, this combination of vacuum and venting provides communication of the severed tissue sample proximally through cutter lumen (52) and into tissue sample holder (40). In addition, engagement between barrel (152) and distal flange (108) of lead screw (102), with resilient assistance from resilient member (154), causes a proximal thread (104) of lead screw (102) to rock cam (110) back to the rearward orientation, as shown in a transition from FIG. 24 to FIG. 11. A cutting stroke will thus be complete, and may be initiated as many times as desired to acquire additional tissue samples.

As noted above, several cutting strokes may be performed to acquire several tissue samples without the user having to withdraw needle (20) from the patient's breast. The user may adjust the orientation of lateral aperture (24) about the axis defined by needle (20) by rotating thumbwheel (202) between cutting strokes for multiple sample acquisition. Once the desired number of tissue samples have been obtained, the user may withdraw needle (20) from the patient's breast. The user may then remove cup (44) from mount (42) and retrieve the tissue samples from filter tray (46).

It should be understood that any of a variety of operations may occur at the end of a cutting stroke. For instance, in versions where the user must hold trigger (35) down during an entire cutting stroke, the user may simply release trigger (35) at the end of the cutting stroke. Biopsy device (10) may provide a variety of forms of feedback to inform the user that a cutting stroke as been completed. By way of example only, biopsy device (10) may provide an electronic beep or other audible indication, a mechanical audible indication (e.g., a loud click), a visual indication (e.g., a light illuminating or flashing), or some other type of audible and/or visual indication. Alternatively, and particularly in versions where cup (44) is transparent, the user may know that a cutting stroke is complete by simply watching tissue sample holder (40) until the user sees a tissue sample being deposited on filter tray (46). Alternatively, a control module may be provided to automatically deactivate motor (36) as soon as a cutting stroke is complete, even if the user continues to hold trigger (35) down. The user may then initiate another cutting stroke by releasing and then re-pressing trigger (35). As yet another merely illustrative example, and as noted above, a control module may initiate a cutting stroke in response to the user briefly pressing or tapping trigger (35), and may automatically deactivate motor (36) as soon as the cutting stroke is complete. The user may then initiate another cutting stroke by briefly pressing or tapping trigger (35) again. As another merely illustrative example, a clutch mechanism may disengage one or more components of cutter rotation mechanism (60) and/or cutter translation mechanism (100), etc., upon completion of a cutting stroke, and require release and re-pressing of trigger (35) to re-engage such components. Still other suitable ways in which biopsy device (10) may operate at the end of a cutting stroke and/or to initiate a subsequent cutting stroke will be apparent to those of ordinary skill in the art in view of the teachings herein.

In versions of biopsy device (10) where an electronic based audible and/or visual indication of the end of a cutting stroke is provided, as well as versions of biopsy device (10) where a control module automatically deactivates motor (36) or disengages a clutch or provides some other type of automated response, there are a variety of ways in which the end of a cutting stroke may be sensed. For instance, a portion of cutter (50) may include a magnet, and a hall effect sensor may be positioned in body (30) to sense the presence of the magnet when cutter (50) reaches the distal-most position at the end of a cutting stroke. As another merely illustrative example, an encoder wheel may be coupled with cutter (50) or a rotating component of cutter rotation mechanism (60), such that the longitudinal position of cutter (50) may be determined based on a number of rotations. Other suitable ways in which the end of a cutting stroke may be sensed (e.g., electronically, mechanically, electro-mechanically, manually, etc.) will be apparent to those of ordinary skill in the art in view of the teachings herein.

Of course, the above examples of use of biopsy device (10) are merely illustrative. Other suitable ways in which biopsy device (10) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:
1. A biopsy device, comprising:
(a) a body;
(b) a needle extending distally from the body, wherein the needle defines a first lumen configured to receive a cutter, wherein the needle further comprises a transverse aperture in communication with the first lumen, the transverse aperture being configured to receive tissue;

(c) a cutter disposed in the first lumen of the needle, wherein the cutter defines a cutter lumen, wherein the cutter is configured to translate within the first lumen to sever tissue protruding through the transverse aperture;

(d) a motor having a drive shaft, wherein the motor is operable to rotate the drive shaft in a first direction; and (e) a cutter translation assembly in communication with the cutter, wherein the cutter translation assembly is operable to translate the cutter proximally in the first lumen in response to rotation of the drive shaft in the first direction, wherein the cutter translation assembly is further operable to translate the cutter distally in the first lumen in response to rotation of the drive shaft in the first direction, wherein the cutter translation assembly comprises a first resilient member operable to bias the cutter translation assembly in the proximal direction and a second resilient member operable to bias the cutter translation assembly in the distal direction.

2. The biopsy device of claim 1, wherein the cutter translation assembly comprises a lead screw.

3. The biopsy device of claim 2, wherein the lead screw is positioned about the cutter and unitarily secured to the cutter.

4. The biopsy device of claim 3, wherein the lead screw comprises a plurality of discrete threads.

5. The biopsy device of claim 2, wherein the cutter translation assembly further comprises a pawl engaged with the lead screw.

6. The biopsy device of claim 5, wherein the pawl is configured to rotate from a first rotational orientation to a second rotational orientation.

7. The biopsy device of claim 6, wherein the cutter translation assembly is operable to translate the cutter proximally in response to rotation of the drive shaft in the first direction when the pawl is positioned in the first rotational orientation.

8. The biopsy device of claim 7, wherein the cutter translation assembly is further operable to translate the cutter distally in response to rotation of the drive shaft in the first direction when the pawl is positioned in the second rotational orientation.

9. The biopsy device of claim 6, wherein the resilient member is configured to rotate the pawl from the first rotational orientation to the second rotational orientation when the cutter reaches a proximal position.

10. The biopsy device of claim 9, wherein the resilient member is grounded to the body, wherein the resilient member is configured to engage the lead screw when the cutter reaches a proximal position to move the pawl from the first orientation to the second orientation.

11. The biopsy device of claim 1, wherein the needle further comprises a second lumen, wherein the second lumen is parallel to the first lumen, wherein the second lumen is in fluid communication with the first lumen via a plurality of openings.

12. The biopsy device of claim 11, further comprising a valve assembly, wherein the valve assembly is configured to switch between pneumatic states comprising:

(i) venting the second lumen to atmosphere, and (ii) sealing the second lumen relative to atmosphere.

13. The biopsy device of claim 12, wherein the valve assembly is responsive to the longitudinal position of the cutter.

14. The biopsy device of claim 13, wherein the valve assembly is configured to vent the second lumen when the cutter is at a distal position, wherein the valve assembly is further configured to substantially seal the second lumen relative to atmosphere when the cutter is at a proximal position, wherein the valve assembly is further configured to substantially seal the second lumen relative to atmosphere when the cutter is at transitional positions between the proximal and distal positions.

15. The biopsy device of claim 13, wherein a portion of the cutter translation assembly is configured to engage a portion of the valve assembly when the cutter is at the distal position, wherein engagement between the portion of the cutter translation assembly and the portion of the valve assembly is configured to reverse the translation direction of the cutter translation assembly.

16. The biopsy device of claim 1, further comprising a cutter rotation assembly, wherein the cutter rotation assembly is in communication with the drive shaft and the cutter, wherein the cutter rotation assembly is operable to rotate the cutter in response to rotation of the drive shaft in the first direction.

17. The biopsy device of claim 1, wherein the motor comprises an electric motor.

18. The biopsy device of claim 1, further comprising a power source and a vacuum source, wherein the power source is in electrical communication with the motor, wherein the vacuum source is in mechanical communication with the motor, wherein the vacuum source is configured to induce a vacuum in the cutter lumen to draw severed tissue samples proximally through the cutter lumen, wherein the power source, the motor, the vacuum source, and the cutter translation assembly are located within the body.

19. A biopsy device, comprising:

(a) a body;

(b) a needle extending distally from the body, wherein the needle defines a tissue receiving aperture;

(c) a cutter, wherein the cutter is configured to translate relative to the needle, wherein the cutter is configured to sever tissue;

(d) a motor having a drive shaft, wherein the motor is operable to rotate the drive shaft in a first direction; and (e) a self-reversing cutter translation assembly in communication with the cutter, wherein the cutter translation assembly is operable to translate the cutter from a distal position to a proximal position in response to rotation of the drive shaft in the first direction, wherein the cutter translation assembly is further operable to translate the cutter from the proximal position to the distal position in response to rotation of the drive shaft in the first direction, wherein the cutter translation assembly comprises a rotatable pawl operable to reverse the translation direction of the cutter, wherein the cutter translation assembly comprises a proximal resilient member operable to rotate the pawl.

20. A biopsy device, comprising:

(a) a body;

(b) a needle extending distally from the body;

(c) a cutter, wherein the cutter is configured to translate relative to the needle, wherein the cutter is configured to sever tissue;

(d) a motor having a drive shaft, wherein the motor is operable to rotate the drive shaft in a first direction;

(e) a self-reversing cutter translation assembly in communication with the cutter, wherein the cutter translation assembly is operable to translate the cutter distally and proximally in response to rotation of the drive shaft in the first direction, the direction of translation being dependent at least in part on the longitudinal position of the cutter, wherein the cutter translation assembly comprises a pawl and a pawl mount, wherein the pawl is rotatable between a first rotational orientation and a second rotational orientation, wherein the rotatable motion of the pawl is restricted by the pawl mount.

\* \* \* \* \*